US010183023B2

(12) United States Patent
Wennogle

(10) Patent No.: US 10,183,023 B2
(45) Date of Patent: Jan. 22, 2019

(54) USES

(71) Applicant: INTRA-CELLULAR THERAPIES, INC., New York, NY (US)

(72) Inventor: Lawrence Wennogle, Hillsborough, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 15/406,346

(22) Filed: Jan. 13, 2017

(65) Prior Publication Data

US 2017/0128453 A1  May 11, 2017

Related U.S. Application Data

(63) Continuation of application No. 14/777,448, filed as application No. PCT/US2014/030412 on Mar. 17, 2014, now Pat. No. 9,545,406.

(60) Provisional application No. 61/799,603, filed on Mar. 15, 2013.

(51) Int. Cl.
*A61K 31/519* (2006.01)
*A61K 31/527* (2006.01)
*A61K 31/53* (2006.01)
*A61K 31/517* (2006.01)
*G01N 33/84* (2006.01)

(52) U.S. Cl.
CPC .......... *A61K 31/519* (2013.01); *A61K 31/517* (2013.01); *A61K 31/527* (2013.01); *A61K 31/53* (2013.01); *G01N 33/84* (2013.01); *G01N 2333/4727* (2013.01); *G01N 2800/28* (2013.01)

(58) Field of Classification Search
None
See application file for complete search history.

(56) References Cited

U.S. PATENT DOCUMENTS

| | | | |
|---|---|---|---|
| 5,202,328 A | 4/1993 | Laszlo et al. | |
| 5,294,612 A | 3/1994 | Bacon et al. | |
| 5,393,755 A | 2/1995 | Neustadt et al. | |
| 5,824,683 A | 10/1998 | McKittrick et al. | |
| 5,849,770 A | 12/1998 | Head et al. | |
| 5,939,419 A | 8/1999 | Tulshlan et al. | |
| 5,962,492 A | 10/1999 | Warrellow et al. | |
| 6,013,621 A | 1/2000 | Nishi et al. | |
| 6,133,273 A | 10/2000 | Gilbert et al. | |
| 6,235,742 B1 | 5/2001 | Bell et al. | |
| 6,235,746 B1 | 5/2001 | Davis et al. | |
| 6,316,444 B1 | 11/2001 | Hunt et al. | |
| 6,423,716 B1 | 7/2002 | Matsuno et al. | |
| 6,492,371 B2 | 12/2002 | Roylance et al. | |
| 6,498,165 B1 | 12/2002 | Armstrong et al. | |
| 6,552,029 B1 | 4/2003 | Davis et al. | |
| 6,586,423 B2 | 7/2003 | Bilodeau et al. | |
| 6,599,908 B1 | 7/2003 | Davis et al. | |
| 6,649,608 B2 | 11/2003 | Pease et al. | |
| 6,670,368 B1 | 12/2003 | Breault et al. | |
| 6,693,099 B2 | 2/2004 | Degenhardt et al. | |
| 6,756,373 B1 | 6/2004 | Allerton et al. | |
| 6,969,719 B2 | 11/2005 | Asberom et al. | |
| 7,153,824 B2 | 12/2006 | Palmer et al. | |
| 7,157,451 B2 | 1/2007 | Atwal et al. | |
| 7,528,148 B2 | 5/2009 | Allen et al. | |
| 7,579,324 B2 | 8/2009 | Burnet et al. | |
| 8,273,750 B2 | 9/2012 | Li et al. | |
| 8,273,751 B2 * | 9/2012 | Li | C07D 487/14 514/257 |
| 8,536,159 B2 | 9/2013 | Li et al. | |
| 8,633,180 B2 | 1/2014 | Li et al. | |
| 8,664,207 B2 | 3/2014 | Li et al. | |
| 8,697,710 B2 | 4/2014 | Li et al. | |
| 8,829,008 B2 | 9/2014 | Li et al. | |
| 8,846,693 B2 | 9/2014 | Li et al. | |
| 8,858,911 B2 | 10/2014 | Li et al. | |
| 8,859,564 B2 | 10/2014 | Li et al. | |
| 8,927,556 B2 | 1/2015 | Li et al. | |
| 9,000,001 B2 | 4/2015 | Li et al. | |
| 9,006,258 B2 | 4/2015 | Fienberg et al. | |
| 9,073,936 B2 | 7/2015 | Li et al. | |
| 9,157,906 B2 | 10/2015 | Greengard et al. | |
| 9,198,924 B2 | 12/2015 | Mates et al. | |
| 9,255,099 B2 | 2/2016 | Li et al. | |
| 9,468,637 B2 | 10/2016 | Fienberg et al. | |
| 9,469,647 B2 | 10/2016 | Li et al. | |

(Continued)

FOREIGN PATENT DOCUMENTS

DE  19931206  1/2001
EP  0063381  10/1982

(Continued)

OTHER PUBLICATIONS

"Anxiety," [retrieved on May 14, 2008]. Retrieved online via Internet, URL: http://www.nim.nih.gov/medlineplus/anxiety.html.
"Autism," [retrieved on May 14, 2008]. Retrieved online via Internet, URL: http://www.nim.nih.gov/medlineplus/autism.html.
Ahn et al. "Potent Tetracyclic Guanine Inhibitors of PDE1 and PDE5 Cyclic Guanosine Monophosphate Phosphodiesterases with Oral Antihypertensive Activity", *J. Med. Chem.*, vol. 40(14), p. 2196-2210, (1997).
Al-Faleq et al., "Heterocyclic o-Aminonitriles: Preparation of Pyrazolo[3,4-d]-pyrimidines with Modification of the substituents at the 1-position", *Molecules*, vol. 6, p. 621-638, (2001).

(Continued)

*Primary Examiner* — Heidi Reese
(74) *Attorney, Agent, or Firm* — Hoxie & Associates LLC

(57) ABSTRACT

The subject matter generally relates to methods of treatment and/or prophylaxis of CNS diseases, disorders, and/or injuries. In one aspect, the subject matter relates to inhibitors of phosphodiesterase 1 (PDE1) as neuroprotective agents and/or neural regenerative agents. In a further aspect, the subject matter relates to individuals that are at risk for the development of CNS disease or disorder.

13 Claims, No Drawings

(56) References Cited

U.S. PATENT DOCUMENTS

| | | | |
|---|---|---|---|
| 9,556,186 | B2 | 1/2017 | Li et al. |
| 9,598,426 | B2 | 3/2017 | Li et al. |
| 9,624,230 | B2 | 4/2017 | Li et al. |
| 2003/0069246 | A1 | 4/2003 | Darrow et al. |
| 2003/0092908 | A1 | 5/2003 | Pitts et al. |
| 2003/0162782 | A1 | 8/2003 | Grossman et al. |
| 2005/0075795 | A1 | 4/2005 | Pandit et al. |
| 2005/0113379 | A1 | 5/2005 | Ge et al. |
| 2008/0176961 | A1 | 7/2008 | Greengard et al. |
| 2008/0193964 | A1 | 8/2008 | Greengard et al. |
| 2008/0194592 | A1 | 8/2008 | Mates et al. |
| 2011/0312978 | A1 | 12/2011 | Davis et al. |
| 2012/0053190 | A1 | 3/2012 | Fienberg et al. |
| 2013/0085123 | A1 | 4/2013 | Li et al. |
| 2013/0324565 | A1 | 12/2013 | Li et al. |
| 2013/0331363 | A1 | 12/2013 | Li et al. |
| 2013/0338124 | A1 | 12/2013 | Li et al. |
| 2014/0005155 | A1 | 1/2014 | Li et al. |
| 2014/0011783 | A1 | 1/2014 | Li et al. |
| 2014/0148421 | A1 | 5/2014 | Li et al. |
| 2014/0194396 | A1 | 7/2014 | Li et al. |
| 2014/0315868 | A1 | 10/2014 | Li et al. |
| 2014/0357606 | A1 | 12/2014 | Li et al. |
| 2015/0038474 | A1 | 2/2015 | Li et al. |
| 2015/0072965 | A1 | 3/2015 | Li et al. |
| 2015/0080357 | A1 | 3/2015 | Li et al. |
| 2015/0197528 | A1 | 7/2015 | Li et al. |
| 2016/0083390 | A1 | 3/2016 | Li et al. |

FOREIGN PATENT DOCUMENTS

| | | |
|---|---|---|
| EP | 0095289 | 11/1983 |
| EP | 0201188 | 12/1986 |
| EP | 0636626 | 2/1995 |
| EP | 0911333 | 4/2002 |
| JP | 53031694 | 3/1978 |
| JP | 2008545783 | 12/2008 |
| JP | 2011506321 | 3/2011 |
| KR | 10-1991-0006866 | 9/1991 |
| WO | WO 1991/019717 | 12/1991 |
| WO | WO 1994/019351 | 9/1994 |
| WO | WO 1998/046606 | 10/1998 |
| WO | WO 1998/052568 | 11/1998 |
| WO | WO 2001/027113 | 4/2001 |
| WO | WO 2002/074312 | 9/2002 |
| WO | WO 2003/002567 | 1/2003 |
| WO | WO 2003/020702 | 3/2003 |
| WO | WO 2003/020724 | 3/2003 |
| WO | WO 2003/042216 | 5/2003 |
| WO | WO 2004/031375 | 4/2004 |
| WO | WO 2004/081563 | 9/2004 |
| WO | WO 2006/133261 | 12/2006 |
| WO | WO 2007/143568 | 12/2007 |
| WO | WO 2007/143705 | 12/2007 |
| WO | WO 2008/063505 | 5/2008 |
| WO | WO 2008/070095 | 6/2008 |
| WO | WO 2009/073210 | 6/2009 |
| WO | WO 2009/075784 | 6/2009 |
| WO | WO 2011/043816 | 4/2011 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |
| WO | WO 2012/171016 | 12/2012 |
| WO | WO 2013/024164 | 2/2013 |
| WO | WO 2013/192556 | 12/2013 |
| WO | WO 2014/145617 | 9/2014 |

OTHER PUBLICATIONS

Aswar et al, "Anti-Cataleptic Activity of Various Extracts of *Ocimum sanctum*", *International Journal of Pharma. Research and Development*, vol. 2, (6), p. 1-7, (2010).

Banker et al., Modern Pharmaceutics, Marcel Dekker, New York (1996).
Bastia et al., Effect of $A_1$ and $A_{2A}$ Adenosine Receptor Ligands in Mouse Acute Models of Pain, *Neuroscience letters*, vol. 328, p. 241-244, (2002).
Bender et al., "Cyclic Nucleotide Phosphodiesterases: Molecular Regulation to Clinical Use", *PharmcoL Rev.*, vol. 58, p. 488-520, (2006).
Blokland et al., "PDE Inhibition and Cognition Enhancement", vol. 22 No. 4, p. 349-354, (2012) (Abstract Only).
Boyd et al., "Dopamine receptor signaling and current and future antipsychotic drugs", *Handb Exp Pharmacol.*, vol. 212, p. 53-86, (2012) doi: 10.1007/978-3-642-25761-2_3.
Burnouf et al., "Synthesis, Structure-Activity Relationships, and Pharmacological Profile of 9-Amino-4-0xo-1-Phenyl-3,4,5,6, 7-Tetrahydrol[I,4]Diazepino[6, 7, 1-hi]lndoles: Discovery of Potent, Selective Phosphodiesterase Type 4 Inhibitors", *J. Med. Chem.*, vol. 43, p. 4850-4867, (2000).
Chalimoniuk et al., "Upregulation of guanylyl cyclase expression and activity in striatum of MPTP-induced parkinsonism in mice" *Biochem Biophys Res Commun.*, vol. 324(1), p. 118-26, (2004).
Chebib et al., "1-Phenylpyrazolo[3,4-d]pyrimidines; Structure-Activity Relationships for C6 Substituents at $A_1$ and $A_{2A}$ Adenosine Receptors", *Bioorganic & Medicinal Chemistry*, vol. 8, p. 2581-2590, (2000).
Chen et al., "Effects of Bimatoprost 0.03% on Ocular Hemodynamics in Normal Tension Glaucoma", *Journal of Ocular Pharmacology and Therpaeutics*, vol. 22(3), p. 188-193, (2006).
Chen et al., "Broad Spectrum neuroprotection profile of phosphodiesterase inhibitos as related to modulation of cell-cucle elements and caspase-3 activation", Neuroscience Letters, vol. 418, p. 165-169, (2007).
Chermat et al., "Adaptation of the Tail Suspension Test to the Rat", *Journal Pharmacology*, vol. 17, p. 348-350, (1986).
Daviglus et al., "National Institutes of Health State-of-the-Science Conference Statement: Preventing Alzheimer Disease and Cognitive Decline", Annals of Internal Medicine, vol. 153 (3), p. 176-185, (2010).
Deshmukh et al., "Amelioration of intracerebroventricular streptozotocin induced cognitive dysfunction and oxidative stress by vinpocetine—a PDE1 inhibitor" *European Journal of Pharmacology*, 620(1-3), p. 49-56, (2009).
Dewald et al., Synthesis and Potential Antipsychotic Activity of 1 H-lmidazo[1.2-c]pyrazolo[3,4-e]pyrimidines, *J. Med. Chem.*, vol. 31, p. 454-461, (1988).
Ehrman et al., "Phosphodiesterase 1B differentially modulates the effects of methamphetamine on locomotor activity and spatial learning through DARPP32-dependent pathways: evidence from PDE1B-DARPP32 double-knockout mice", *Genes Brain Behav.*, vol. 5, p. 540-51, (2006).
Fienberg et al., "DARPP-32: Regulator of the Efficacy of Dopaminergic Neurotransmission", *Science*, vol. 281, p. 838-842, (1998).
Filgueiras et al., "Phosphodiesterase type 1 inhibition improves learning in rats exposed to alcohol during the third trimester equivalent of human gestation" *Neuroscience Letters*, vol. 473(3), p. 202-207, (2010).
Gelbin et al., "Ketene-S, N-acetals as synthons for heterocycles new synthesis of pyrimidinones", *Journal Fuer Praktische Chemie*, vol. 329(5), p. 753-766, (1987).
Goodman & Gilman, The Pharmacological Basis of Therapeutics, McGraw-Hill Interamericana, p. 892, (2007).
Greengard et al., "Beyond the Dopamine Receptor: the DARPP-32 Protein Phosphatase-1 Cascade", *Neuron*, vol. 23, p. 435,447, (1999).
Han et al., "The Calcium/Calmodulin-dependent Phosphodiesterase PDE1C Downregulates Glucose-induced Insulin Secretion", *J. Bio. Chem.*, vol. 274(32), p. 22337-22344, (1999).
Hulley et al., "Cyclic AMP promotes the survival of dopaminergic neurons in vitro and protects them from the toxic effects of MPP+", *J Neural Transm Suppl.*, vol. 46, p. 217-28, (1995).
International Search Report of International Application No. PCT/US2006/022066, dated Apr. 3, 2007, 1 page.

(56) References Cited

OTHER PUBLICATIONS

International Search Report of International Application No. PCT/US2008/013411, dated Mar. 19, 2009, 2 pages.
International Search Report of International Application No. PCT/US2014/030412, dated Nov. 6, 2014, 3 pages.
Jiang et al., Chemoenzymatic Asymmetric Total Synthesis of Phosphodiesterase Inhibitors: Preparation of a Polycyclic Pyrazolo[3,4-d]pyrimidine from an Acylnitroso Oiels-Alder Cycloadduct-Derived Aminocyclopentenol, *J. Org. Chem.*, vol. 70, p. 2824-2827 (2004).
Kakkar et al. "Amantadine: an antiparkinsonian agent inhibits bovine brain 60 kDa calmodulin-dependent cyclic nucleotide phosphodiesterase isozyme", *Brain Res.*, vol. 749(2), p. 290-4, (1997).
Kakkar et al. "Calmodulin-dependent cyclic nucleotide phosphodiesterase (PDE1)" *Cell Mol Life Sci.*, vol. 55(8-9), p. 1164-86, (1999).
Kakkar et al., "Inhibition of Bovine Brain Calmodulin-Dependent Cyclic Nucleotide Phosphodiesterase Isozymes by Deprenyl", *Life Sciences*, vol. 59(21), p. 337-341, (1996).
Klaissle et al., "Physical activity and environmental enrichment regulate the generation of neural precursors in the adult mouse substantia nigra in a dopamine-dependent manner" *BMC Neurosci.*, vol. 13(132), p. 1-15, (2012); doi: 10.1186/1471-2202-13-132.
Kleppisch et al., "Phosphodiesterases in the central nervous system" *Handb Exp Pharmacol.* 2009;(191):71-92. doi: 10.1007/978-3-540-68964-5_5.
Laddha et al., "A new therapeutic approach in Parkinson's disease: Some novel quinazoline derivatives as dual selective phosphodiesterase 1 inhibitors and anti-inflammatory agents" *Bioorganic & Medicinal Chemistry*, vol. 17(19), p. 6796-6802, (2009).
Lundqvist et al., Exploitation of Structural and Regulatory Diversity in Glutamate Racemases, *Nature*, vol. 447, p. 817-822, (2007).
Mani et al., "Requirement for DARPP-32 in Progesterone-Facilitated Sexual Receptivity in Female Rats and Mice", *Science*, vol. 287, p. 1053-1056, (2000).
Medina et al., "Therapeutic Utility of Phosphodiesterase Type 1 Inhibitors in Neurological Conditions", *Front. Neurosci.*, vol. 5(21), 6 pages, (2011).
Murray et al., "Expression and activity of cAMP phosphodiesterase isoforms in pulmonary artery smooth muscle cells from patients with pulmonary hypertension: role for PDE1", *Am. J. Physiol. Lunr:l Cell Mol. Physiol.*, vol. 292, p. L294-L303, (2007).
Murray et al., LY503430, a Novel _-Amlno-3-hydroxy-5-methylisoxazole-4-proplonlc Acid Receptor Potentiator with Functional, Neuroprotective and Neurotrophic Effects In Rodent Models of Parkinson's Disease, *J. Pharmacol & Experim. Thera.*, vol. 306(2), p. 752-762, (2003).
Nishi et al., "Advanced Research on Dopamine Signaling to Develop Drugs for the Treatment of Mental Disorders: Biochemical and Behavioral Profiles of Phosphodiesterase Inhibition in Dopaminergic Neurotransmission", *J. Pharmacol. Sci.*, vol. 114, p. 6-16, (2010).
Noguchi et al, "A Facile Preparation of 7-(substituted amino-)-6H-pyrrolo[3,4-d]-pyrimidine Derivatives"; *Bulletin Chem. Soc. of Japan*, vol. 62(9), p. 3043-5; (1989).
Pardo et al., "Synthesis of 1-(p-nitrobenzyl)azoles and 1-(p-nitrobenzyl)benzazoles", *Opp Briefs*, vol. 32(4), p. 385-390, (2000).
Park et al., "Traumatic Brain Injury: Can the consequences be stopped?" *CMAJ*, vol. 178(9), p. 1163-1170, (2008).
Polli et al., "Expression of a Calmodulin-Dependent Phosphodiesterase Isoform (PDE1 B1) Correlates With Brain Regions Having Extensive Dopaminergic Innervation," *The Journal of Neuroscience*, vol. 14(3), p. 1251-1261, (1994).
Porsolt et al., *Nature*, vol. 266, p. 730-732, (1977).
Poulsen et al., "High-Pressure Synthesis of Enantiomerlcally Pure C-6 Substituted Pyrazolo[3,4-d]pyrimidines", *Bioorganic & Medicinal Chemistry letter*, vol. 11, p. 191-193, (2001).

Reed et al., "Phosphodiesterase 1 B Knock-Out Mice Exhibit Exaggerated Locomotor Hyperactivity and DARPP-32 Phosphorylation in Response to Dopamine Agonists and Display Impaired Spatial Learning", *The Joumal of Neuroscience*, vol. 22(12), p. 5188-5197, (2002).
Rybalkin et al., "Cyclic GMP Phosphodiesterases and Regulation of Smooth Muscle Function", *Circ. Res.*, vol. 93, p. 280-291, (2003).
Schmidt et al., "Phosphodiesterase inhibitors as potential cognition enhancing agents" *Current Topics in Medicinal Chemistry*, vol. 10(2), p. 222-230, (2010).
Sharma et al., "Regulation of Calmodulin-Stimulated Cyclic Nucleotide Phosphodiesterase (PDE1): Review", *International Journal of Molecular Medicine*, vol. 18, p. 95-105 (2006).
Shimizu et al., "Calmodulin-Dependent Cyclic Nucleotide Phosphodiesterase (PDE1) Is a Pharmacological Target of Differentiation-Inducing Factor-1, an Antitumor Agent Isolated from Dictyostelium", *Cancer Research*, vol. 64, p. 2568-2571, (2004).
Shook, et al. "Design and Characterization of Optimized Adenoside $A_{2A}/A_1$ Receptor Antagonists for the Treatment of Parkinson's Disease", *J. Med. Chem.*, p. 1-47 (2012).
Silva et al., "Advances in Prodrug Design", Mini-Reviews in Medicinal Chemistry, vol. 5, p. 893-914, (2005).
Takahashi et al., "Measurement of Intracellular Calcium", *Physiological Reviews*, vol. 79(4), p. 1089-1125, (1999).
Turko et al., Inhibition of Cyclic GMP-Binding Cyclic GMP-Specific Phosphodiesterase (Type 5) by Sildenafil and Related Compounds, *Molecular Pharmacology*, vol. 56, p. 124-130, (1999).
Ungerstedt et al., "Stereotaxic Mapping of the Monoamine Pathways in the Rat Brain", *Acta Physiology Second Suppl.*, vol. 367, p. 1-48, (1971).
Ungerstedt et al., "Quantitative Recording of Rotational Behavior in Rtas After 6-Hydroxy-Dopamine Lesions of the Nigrostriatal Dopamine System", *Brain Research*, vol. 24, p. 485-493, (1970).
Vatter et al., "Differential Phosphodiesterase Expression and Cytosolic Ca2+ in Human CNS Tumour Cells and in Non-Malignant and Malignant Cells of Rat Origin", *J. of Neurochemistry*, vol. 93, p. 321-329 (2005).
Wolff et al., Manfred E., Burger's Medicinal Chemistry and Drug Discovery, Fifth Ed., vol. 1: Principles and Practice, John Wiley & Sons, p. 975, (1995).
Xia et al., Synthesis and Evaluation of Polycyclic Pyrazolo[3,4-d]pyrimidines as PDE1 and PDE5 cGMP Phosphodiesterase Inhibitors, *J. Med. Chem.*, vol. 40, p. 4372-77, (1997).
Ennaceur et al., "A new one-trial test for neurobiological studies of memory in rats. 1: Behavioral data," *Behavioral Brain Research*, vol. 31, p. 47-59 (1988).
Ghorab et al., "Synthesis, Anticancer and Radioprotective Activities of Some New Pyrazolo[3,4-d]pyrimidines Containing Amino Acid Moieties," *Arzneimittelforschung*, vol. 59(2), p. 96-103 (2009).
International Search Report of International Application No. PCT/US2014/025666, dated Jul. 7, 2014, 3 pages.
Ji H-M et al., "Efficacy of vinpocetine on neuropathy in patients with type 2 diabetes mellitus," *Chinese Journal of New Drugs*, vol. 18(15), Abstract (2009).
Patani et al., "Bioisosterism: A Rational Approach in Drug Design," *Chemical Reviews*, vol. 96(8), p. 3147-3716 (1996).
Prickaerts et al., "Possible role of nitric oxide-cyclic GMP pathway in object recognition memory: Effects of 7-nitroindazole and zaprinast," *European Journal of Pharmacology*, vol. 337, p. 125-136 (1997).
Takimoto et al., "Controlling Myocyte cGMP. Phosphodiesterase 1 Joins the Fray," *Circulation Research*, vol. 105, p. 931-933 (2009).
Youdim, "The Path from Anti Parkinson Drug Selegiline and Rasagiline to Multi-functional Neuroprotective Anti Alzheimer Drugs Ladostigil and M30," *Current Alzheimer Research*, vol. 3, p. 541-550 (2006).

\* cited by examiner

USES

CROSS REFERENCE TO RELATED APPLICATIONS

This Application is a U.S. continuation application of U.S. application Ser. No. 14/777,448, filed Sep. 15, 2015, which is a U.S. National Stage application of PCT/US2014/030412, filed Mar. 17, 2014, which claims the benefit of U.S. Provisional Application 61/799,603, filed on Mar. 15, 2013, the contents of each of which are herein incorporated by reference in their entirety.

FIELD OF THE INVENTION

The field generally relates to methods of treatment and/or prophylaxis of CNS diseases, disorders, and/or injuries. In one aspect, the field relates to inhibitors of phosphodiesterase 1 (PDE1) as neuroprotective agents and/or neural regenerative agents. In a further aspect, the field relates to prevent the development of a CNS disease or disorder in an individual at risk for the development of a CNS disease or disorder.

BACKGROUND OF THE INVENTION

Eleven families of phosphodiesterases (PDEs) have been identified but only PDEs in Family I, the Ca2+-calmodulin-dependent phosphodiesterases (CaM-PDEs), which are activated by the Ca2+-calmodulin and have been shown to mediate the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of opaminergic innervation. Although PDE1B is primarily expressed in the central nervous system, it may be detected in the heart. PDE1C is expressed in olfactory epithelium, cerebellar granule cells, striatum, heart, and vascular smooth muscle.

Neurogenesis is a vital process in the brains of animals and humans, whereby new nerve cells are continuously generated throughout the life span of the organism. The newly born cells are able to differentiate into functional cells of the central nervous system and integrate into existing neural circuits in the brain. Neurogenesis is known to persist throughout adulthood in two regions of the mammalian brain: the subventricular zone (SVZ) of the lateral ventricles and the dentate gyrus of the hippocampus. In these regions, multipotent neural progenitor cells (NPCs) continue to divide and give rise to new functional neurons and glial cells (for review Gage 2000). It has been shown that a variety of factors can stimulate adult hippocampal neurogenesis, e.g., adrenalectomy, voluntary exercise, enriched environment, hippocampus dependent learning and antidepressants (Yehuda 1989, van Praag 1999, Brown J 2003, Gould 1999, Malberg 2000, Santarelli 2003). Other factors, such as adrenal hormones, stress, age and drugs of abuse negatively influence neurogenesis (Cameron 1994, McEwen 1999, Kuhn 1996, Eisch 2004).

While the importance of neurogenesis cannot be overstated, the failure of axons to regenerate after spinal cord injury still remains one of the greatest challenges facing both medicine and neuroscience. An important development, however, has been the identification of inhibitory proteins in CNS myelin. One problem that causes the failure of CNS neuron regeneration is inhibition of neurite outgrowth by certain bioactive molecules. Myelin contributes to a number of proteins that have shown to inhibit neurite process outgrowth. NogoA is the first protein identified on the surface of the oligodendrocytes and some axons. Other proteins that can contribute to inhibition include myelin-associated glycoprotein (MAG), oligodendrocyte-myelin glycoprotein (OMgp) and the proteoglycan versican.

It is believed that the central nervous system (CNS) environment could limit axonal regeneration after injury. Indeed, CNS myelin has been identified as a major factor contributing to regenerative failure. There are those in the field that believe, and have provided evidence, that CNS myelin contains proteins that inhibit axonal growth.

Various strategies have been proposed for overcoming myelin inhibition. One strategy that has been effective has been to elevate the levels of intracellular cAMP. Some manners in which this may be done include: a peripheral conditioning lesion, administration of cAMP analogues, priming with neurotrophins or treatment with the phosphodiesterase inhibitor rolipram (PDE4 inhibitor). The effects of cAMP may be transcription dependent, and cAMP-mediated activation of CREB may lead to upregulation and expression of genes such as arginase I and interleukin-6. The products of these genes are believed to promote axonal regeneration, which raises the possibility that other cAMP-regulated genes could yield additional agents that would be beneficial in the treatment of spinal cord injury. However, with regard to increasing the expression of IL-6, one significant disadvantage to this mechanism of action may be that IL-6 is a potentially harmful pro-inflammatory cytokine, meaning, it is possible that high levels of IL-6 could actually exacerbate the inflammation that occurs after spinal cord injury which could then lead to increase in cell death. Indeed, a factor supporting this concern is that IL-6 transgenic mice have been observed to have extensive astrogliosis, neurodegeneration, and breakdown of the blood brain barrier.

SUMMARY OF THE INVENTION

It is an advantage of the present invention that a PDE1 inhibitor (e.g., a compound of any of Formula I-XI) may act as a neuroprotective agent and/or neuroregenerative agent. In the event of a CNS injury (e.g., spinal cord injury), disease, or disorder, the compounds and methods disclosed herein may be employed to aid or enhance neurite outgrowth and axonal regeneration even in the presence of myelin inhibitors.

Without being bound by any particular theory, it is believed to be at least one advantage of the present invention that the administration of a PDE1 inhibitor (e.g., any compound of Formula I-XI) may act to increase levels of intracellular cAMP and initiate the transcription of genes that are necessary for overcoming myelin inhibitors and promoting neurite outgrowth and/or axonal regeneration in the case of a CNS disease, disorder, or injury.

Furthermore, it is believed to be an advantage that the administration of a PDE1 inhibitor (e.g., a compound of any of Formula I-XI) may elevate the intracellular levels of both cAMP as well as cGMP. Without being bound by theory, this rise in both cAMP and cGMP may serve as a counterbalance to the potentially detrimental effects that may be associated with chronically elevated levels of intracellular calcium. It has been observed that elevated levels of intracellular calcium could have some type of involvement in the development of various degenerative diseases. For instance, one possible explanation is that elevated levels of intracellular calcium (e.g., chronically elevated levels of intracellular calcium) could lead to the activation of PDE1 by calmodulin which would have a negative effect on the expression of cAMP.

However, without being bound by any theory, it is believed that one potential benefit of the administration of a PDE1 inhibitor (e.g., a compound of any of Formula IXI) is that this may lead to not only an increase in cAMP, but also cGMP. This increase in intracellular cGMP may lead to an increase in the activity of PKG, preventing a further rise in intracellular calcium levels. Thus, without being bound by any theory, the administration of a PDE1 inhibitor (e.g., a compound of any of Formula I-XI) could have the dual benefit of, for example, playing a beneficial role in axonal regeneration (and/or being neuroprotective) while simultaneously decreasing or lessening the degenerative effects that are possibly associated with elevated intracellular calcium levels.

In one embodiment the invention comprises compositions and methods to treat or prevent a CNS disease, disorder, or injury (e.g., spinal cord injury, e.g., spinal muscular atrophy, e.g., motor neuron injury), wherein the method comprises administration of an effective amount of a PDE1 inhibitor (e.g., a compound of any of Formula I-XI) to modulate intracellular levels of cAMP. In one embodiment, this increase in intracellular cAMP is neuroprotective and/or aids in the increase or stimulation of neurogenesis (e.g., the PDE1 inhibitor increases neurite outgrowth and/or axonal regeneration).

In still a further embodiment the invention comprises compositions and methods to treat or prevent injuries to the peripheral nervous system (PNS) wherein the method comprises administration of a PDE1 inhibitor to increase intracellular levels of cAMP which (either directly or indirectly) increases nerve regeneration and/or is protective against further nerve damage.

In one embodiment the invention comprises compositions and methods to prevent a CNS disease or disorder in a subject that is at risk for developing said disease or disorder, wherein the method comprises:
1.) Obtaining a sample from the subject;
2.) Measuring the levels of intracellular calcium from the sample;
3.) Comparing the levels of intracellular calcium in the biological sample to a reference standard;
4.) Determining whether a patient is at risk for developing a CNS disease or disorder based upon the level of intracellular calcium compared to the reference standard;
5.) Administering a PDE1 inhibitor (e.g., a compound of any of Formula I-XI) to a subject based upon the subject's levels of intracellular calcium (e.g., administration of a PDE1 inhibitor to a subject because they have elevated intracellular calcium levels compared to the reference standard).

DETAILED DESCRIPTION OF THE INVENTION

Compounds for Use in the Methods of the Invention

In one embodiment, the PDE1 inhibitors for use in the methods of treatment and prophylaxis described herein are optionally substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., a Compound of Formula II, e.g., II-A or II-B:

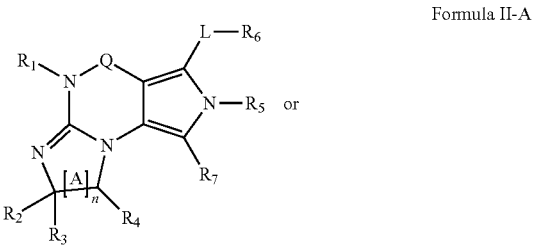

Formula II-A

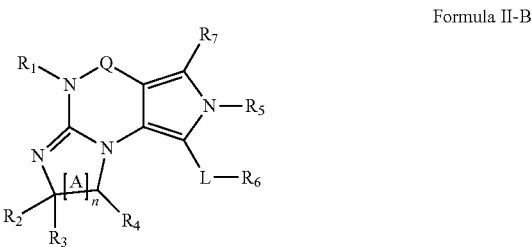

Formula II-B wherein
(i) Q is C(=O), C(=S), C(=N(R$_{20}$)) or CH$_2$;
(ii) L is a single bond, —N(H)—, —CH$_2$—, —S—, —S(O)— or —S(O$_2$)—;
(iii) R$_1$ is H or C$_{1-4}$ alkyl (e.g., methyl);
(iv) R$_4$ is H or C$_{1-6}$ alkyl (e.g., methyl or isopropyl) and R$_2$ and R$_3$ are, independently,
H
C$_{1-6}$alkyl (e.g., methyl, isopropyl) optionally substituted with halo or hydroxy (e.g., R$_2$ and R$_3$ are both methyl, or R$_2$ is H and R$_3$ is methyl, ethyl, isopropyl or hydroxyethyl),
aryl,
heteroaryl,
(optionally hetero)arylalkoxy,
(optionally hetero)arylC$_{1-6}$alkyl; or
R$_2$ and R$_3$ together form a 3- to 6-membered ring;
or
R$_2$ is H and R$_3$ and R$_4$ together form a di-, tri- or tetramethylene bridge (pref. wherein the R$_3$ and R$_4$ together have the cis configuration, e.g., where the carbons carrying R$_3$ and R$_4$ have the R and S configurations, respectively);
or
(v) R$_5$ is
a) -D-E-F, wherein:
D is C$_{1-4}$alkylene (e.g., methylene, ethylene or prop-2-yn-1-ylene);
E is a single bond, C$_2$-4alkynylene (e.g., —C≡C—), arylene (e.g., phenylene) or heteroarylene (e.g., pyridylene);
F is
H,
aryl (e.g., phenyl),
heteroaryl (e.g., pyridyl, diazolyl, triazolyl, for example, pyrid-2-yl, imidazol-1-yl, 1,2,4-triazol-1-yl),
halo (e.g., F, Br, Cl),
haloC$_{1-4}$alkyl (e.g., trifluoromethyl),
—C(O)—R$_{15}$,
—N(R$_{16}$)(R$_{17}$), or $C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);

wherein D, E and F are independently and optionally substituted with one or more halo (e.g., F, Cl or Br), $C_{1-4}$alkyl (e.g., methyl), halo$C_{1-4}$alkyl (e.g., trifluoromethyl), $C_{1-4}$alkoxy (e.g., methoxy), hydroxy, $C_{1-4}$carboxy, or an additional aryl or heteroaryl (e.g., biphenyl or pyridylphenyl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-4}$alkyl (e.g., 5-trifluoromethylpyrid-2-yl) or $C_{1-4}$alkyl (e.g., 5-methylpyrid-2-yl), or F is aryl, e.g., phenyl, substituted with one or more halo (e.g., 4-fluorophenyl) or F is a $C_{3-7}$heterocycloalkyl (e.g., pyrrolidinyl) optionally substituted with a $C_{1-6}$alkyl (e.g., 1-methylpyrrolidin-3-yl); or b) a substituted heteroarylalkyl, e.g., substituted with halo$C_{1-4}$alkyl;

c) attached to the nitrogen on the pyrrolo portion of Formula II-A or II-B and is a moiety of Formula A

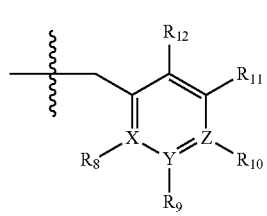

Formula A wherein X, Y and Z are, independently, N or C, and $R_8$, $R_9$, $R_{11}$ and $R_{12}$ are independently H or halogen (e.g., Cl or F), and $R_{10}$ is halogen,
$C_{1-4}$alkyl,
halo$C_{1-4}$alkyl (e.g., triflouromethyl)
$C_{1-4}$alkoxy (e.g. methoxy),
$C_{3-7}$cycloalkyl,
hetero$C_{3-7}$cycloalkyl (e.g., pyrrolidinyl or piperidinyl),
$C_{1-4}$haloalkyl (e.g., trifluoromethyl),
aryl (e.g., phenyl),
heteroaryl (e.g., pyridyl (for example pyrid-2-yl or pyrid-4-yl), or thiadiazolyl (e.g., 1,2,3-thiadiazol-4-yl)), diazolyl (e.g., imidazol-1-yl), triazolyl (e.g., 1,2,4-triazol-1-yl), tetrazolyl,
arylcarbonyl (e.g., benzoyl),
alkylsulfonyl (e.g., methylsulfonyl),
heteroarylcarbonyl, or
alkoxycarbonyl;

wherein the aryl, heteroaryl, cycloalkyl or heterocycloalkyl is independently, optionally substituted with one or more $C_{1-4}$alkyl (e.g., methyl), halogen (e.g., chloro or fluoro), halo$C_{1-4}$alkyl (e.g., trifluoromethyl), hydroxy, $C_{1-4}$carboxy, —SH or an additional aryl, heteroaryl (e.g., biphenyl or pyridylphenyl) or $C_{3-8}$cycloalkyl, preferably $R_{10}$ is phenyl, pyridyl, piperidinyl or pyrrolidinyl optionally substituted with the substituents previously defined, e.g. optionally substituted with halo or alkyl provided that when X, Y, or Z is nitrogen, $R_8$, $R_9$, or $R_{10}$, respectively, is not present;

(vi) $R_6$ is

H,
$C_{1-4}$alkyl (e.g., methyl, ethyl, n-propyl, isobutyl),
$C_{3-7}$cycloalkyl (e.g., cyclopentyl or cyclohexyl),
hetero$C_{3-7}$cycloalkyl (e.g., pyrrolidinyl, piperidinyl, morpholinyl),
aryl (e.g., phenyl),
heteroaryl (e.g., pyrid-4-yl),
aryl$C_{1-4}$alkyl (e.g., benzyl),
arylamino (e.g., phenylamino),
heteroarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$), wherein the aryl and heteroaryl are optionally substituted with one or more $C_{1-4}$alkyl (e.g., methyl), halogen (e.g., chloro or fluoro), halo$C_{1-4}$alkyl (e.g., trifluoromethyl), hydroxy, $C_{1-4}$carboxy, or an additional aryl, heteroaryl (e.g., biphenyl or pyridylphenyl) or $C_3$-8cycloalkyl;

(vii) $R_7$ is H, $C_{1-6}$alkyl (e.g., methyl or ethyl), halogen (e.g., Cl), —N($R_{18}$)($R_{19}$), hydroxy or $C_{1-6}$alkoxy;

(viii) n=0 or 1;

(ix) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy, (optionally hetero)aryl$C_{1-4}$alkyl or $R_{14}$ can form a bridge with $R_2$ or $R_4$;

(x) $R_{15}$ is $C_{1-4}$alkyl, halo$C_{1-4}$alkyl, —OH or —O$C_{1-4}$alkyl (e.g., —OCH$_3$)

(xi) $R_{1-6}$ and $R_{17}$ are independently H or $C_{1-4}$alkyl;

(xii) $R_{18}$ and $R_{19}$ are independently

H,
$C_{1-4}$alky (e.g., methyl, ethyl, n-propyl, isobutyl),
$C_{3-8}$cycloalky (e.g., cyclohexyl or cyclopenyl), hetero$C_{3-8}$cycloalky (e.g., pyrrolidinyl, piperidinyl, morpholinyl), aryl (e.g., phenyl) or
heteroaryl (e.g., pyridyl), wherein said aryl and heteroaryl are optionally substituted with one or more halo (e.g., fluorophenyl, e.g., 4-fluorophenyl),
hydroxy (e.g., hydroxyphenyl, e.g., 4-hydroxyphenyl or 2-hydroxyphenyl),
$C_{1-4}$alkyl (e.g., methyl),
halo$C_{1-4}$alkyl (e.g., trifluoromethyl),
$C_{1-4}$carboxy, or
an additional aryl, heteroaryl (e.g., biphenyl or pyridylphenyl) or $C_{3-8}$cycloalkyl, (xiii) $R_{20}$ is H, $C_{1-4}$alkyl or $C_{3-7}$cycloalkyl;

in free or salt form.

In another embodiment, the PDE1 inhibitors for use in the methods of treatment and prophylaxis described herein are Compound of Formula I, e.g. Formula I-A and I-B:

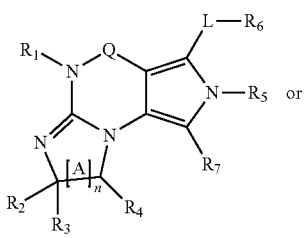

Formula I-A

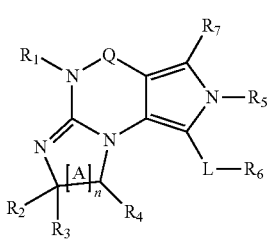

Formula I-B wherein
(i) Q is C(=O), C(=S), C(=N(R$_{20}$)) or CH$_2$;
(ii) L is a single bond, —N(H)—, —CH$_2$—, —S—, —S(O)— or —S(O$_2$)—;
(iii) R$_1$ is H or C$_{1-4}$ alkyl (e.g., methyl);
(iv) R$_4$ is H or C$_{1-6}$ alkyl (e.g., methyl or isopropyl) and R$_2$ and R$_3$ are, independently,
H or C$_{1-6}$alkyl (e.g., methyl, isopropyl) optionally substituted with halo or hydroxy (e.g., R$_2$ and R$_3$ are both methyl, or R$_2$ is H and R$_3$ is methyl, ethyl, isopropyl or hydroxyethyl),
aryl,
heteroaryl,
(optionally hetero)arylalkoxy, or
(optionally hetero)arylC$_{1-6}$alkyl;
or
R$_2$ is H and R$_3$ and R$_4$ together form a di-, tri- or tetramethylene bridge (pref. wherein the R$_3$ and R$_4$ together have the cis configuration, e.g., where the carbons carrying R$_3$ and R$_4$ have the R and S configurations, respectively);
(v) R$_5$ is
a) -D-E-F, wherein:
D is C$_{1-4}$alkylene (e.g., methylene, ethylene or prop-2-yn-1-ylene);
E is a single bond, C$_2$-4alkynylene (e.g., —C≡C—), arylene (e.g., phenylene) or heteroarylene (e.g., pyridylene);
F is
H,
aryl (e.g., phenyl),
heteroaryl (e.g., pyridyl, diazolyl, triazolyl, for example, pyrid-2-yl, imidazol-1-yl, 1,2,4-triazol-1-yl),
halo (e.g., F, Br, Cl),
haloC$_{1-4}$alkyl (e.g., trifluoromethyl),
—C(O)—R$_{15}$,
—N(R$_{16}$)(R$_{17}$), or
C$_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more halo (e.g., F, Cl or Br), C$_{1-4}$alkyl (e.g., methyl), haloC$_{1-4}$alkyl (e.g., trifluoromethyl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), haloC$_{1-4}$alkyl (e.g., 5-trifluoromethylpyrid-2-yl) or C$_{1-4}$alkyl (e.g., 5-methylpyrid-2-yl), or F is aryl, e.g., phenyl, substituted with one or more halo (e.g., 4-fluorophenyl) or F is a C$_{3-7}$heterocycloalkyl (e.g., pyrrolidinyl) optionally substituted with a C$_{1-6}$alkyl (e.g., 1-methylpyrrolidin-3-yl); or
b) a substituted heteroarylalkyl, e.g., substituted with haloalkyl;
c) attached to the nitrogen on the pyrrolo portion of Formula I-A or I—B and is a moiety of Formula A

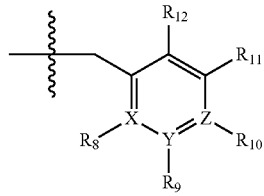

Formula A wherein X, Y and Z are, independently, N or C, and
R$_8$, R$_9$, R$_{11}$
and R$_{12}$ are independently H or halogen (e.g., Cl or F), and R$_{10}$ is
halogen,
C$_{1-4}$alkyl,
C$_{3-7}$cycloalkyl,
C$_{1-4}$haloalkyl (e.g., trifluoromethyl),
aryl (e.g., phenyl),
heteroaryl (e.g., pyridyl (for example pyrid-2-yl), or thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
provided that when X, Y, or Z is nitrogen, R$_8$, R$_9$, or R$_{10}$, respectively, is not present;
(vi) R$_6$ is
H,
C$_{1-4}$alkyl,
C$_{3-7}$cycloalkyl (e.g., cyclopentyl),
aryl (e.g., phenyl),
heteroaryl (e.g., pyrid-4-yl),
arylC$_{1-4}$alkyl (e.g., benzyl),
arylamino (e.g., phenylamino),
heteroarylamino,
N,N-diC$_{1-4}$alkylamino,
N,N-diarylamino,
N-aryl-N-(arylC$_{1-4}$alkyl)amino (e.g., N-phenyl-N-(1,1'-biphen-4-ylmethyl)amino), or
—N(R$_{18}$)(R$_{19}$);
wherein the aryl or heteroaryl is optionally substituted with one or more halo (e.g., F, Cl), hydroxy or C$_{1-6}$alkoxy;
(vii) R$_7$ is H, C$_{1-6}$alkyl, halogen (e.g., Cl), —N(R$_8$)(R$_{19}$);
(viii) n=0 or 1;

(ix) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy or (optionally hetero)aryl$C_{1-4}$alkyl;

(x) $R_{15}$ is $C_{1-4}$alkyl, halo$C_{1-4}$alkyl, —OH or —O$C_{1-4}$alkyl (e.g., —$OCH_3$)

(xi) $R_{16}$ and $R_{17}$ are independently H or $C_{1-4}$alkyl;

(xii) $R_{18}$ and $R_{19}$ are independently H, $C_{1-4}$alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl)

(xiii) $R_{20}$ is H, $C_{1-4}$alkyl or $C_{3-7}$cycloalkyl;

in free or salt form.

The invention further provides optionally substituted 4,5,7,8-tetrahydro- (optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, in free or salt form, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazolo[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4(5H)-thione or 7,8-dihydro-2H-imidazo[1,2-a]pyrazolo[4,3-e]pyrimidine-4(5H)-thione compounds, e.g., a Compound of Formula III:

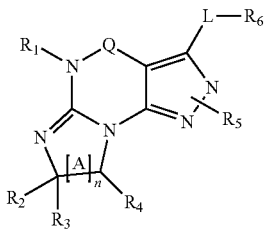

Formula III wherein (xiv) Q is C(=S), C(=N($R_{20}$)) or $CH_2$;

(xv) L is a single bond, —N(H)—, —$CH_2$—;

(xvi) $R_1$ is H or $C_{1-4}$ alkyl (e.g., methyl or ethyl);

(xvii) $R_4$ is H or $C_{1-6}$ alkyl (e.g., methyl, isopropyl) and $R_2$ and $R_3$ are, independently:

H or $C_{1-6}$alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl), aryl, heteroaryl, (optionally hetero)arylalkoxy, (optionally hetero)aryl$C_{1-6}$alkyl, or $R_2$ and $R_3$ together form a 3- to 6-membered ring;

or $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);

(xviii) $R_5$ is d) -D-E-F, wherein:

D is $C_{1-4}$alkylene (e.g., methylene, ethylene or prop-2-yn-1-ylene);

E is a single bond, $C_2$-4alkynylene (e.g., —C≡C—), arylene (e.g., phenylene) or heteroarylene (e.g., pyridylene);

F is

H, aryl (e.g., phenyl), heteroaryl (e.g., pyridyl, diazolyl, triazolyl, for example, pyrid-2-yl, imidazol-1-yl, 1,2,4-triazol-1-yl), halo (e.g., F, Br, Cl), halo$C_{1-4}$alkyl (e.g., trifluoromethyl),

—C(O)—$R_{15}$,

—N($R_{16}$)($R_{17}$),

—S(O)$_2R_{21}$ or $C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);

wherein D, E and F are independently and optionally substituted with one or more:

halo (e.g., F, Cl or Br), $C_{1-4}$alkyl (e.g., methyl), halo$C_{1-4}$alkyl (e.g., trifluoromethyl), $C_{1-4}$alkoxy) or $C_{1-4}$alkyl (e.g., 5-methylpyrid-2-yl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), or F is aryl, e.g., phenyl, substituted with one or more halo (e.g., 4-fluorophenyl)

or F is a $C_{3-7}$heterocycloalkyl (e.g., pyrrolidinyl) optionally substituted with a $C_{1-6}$alkyl (e.g., 1-methylpyrrolidin-3-yl);

or e) a substituted heteroarylalkyl, e.g., substituted with haloalkyl;

f) attached to one of the nitrogens on the pyrazolo portion of Formula III and is a moiety of Formula A

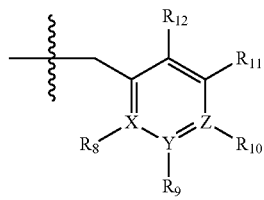

Formula A wherein X, Y and Z are, independently, N or C, and $R_8$, $R_9$, $R_{11}$ and $R_{12}$ are independently H or halogen (e.g., Cl or F), and $R_{10}$ is:

halogen, $C_{1-4}$alkyl, $C_{3-7}$cycloalkyl, het$C_{3-7}$cycloalkyl (e.g., pyrrolidinyl or piperidinyl), $C_{1-4}$haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl),
alkylsulfonyl (e.g., methylsulfonyl),
heteroarylcarbonyl, or
alkoxycarbonyl;
  wherein the aryl, heteroaryl, cycloalkyl or heterocloalkyl is independently and optionally substituted with one or more halo (e.g., F or Cl), $C_{1-4}$alkyl, $C_{1-4}$alkoxy, $C_{1-4}$haloalkyl (e.g., trifluoromethyl), —SH;
  preferably $R_{10}$ is phenyl, pyridyl, piperidinyl or pyrrolidinyl optionally substituted with the substituents previously defined, e.g. optionally substituted with halo or alkyl
  provided that when X, Y, or Z is nitrogen, $R_8$, $R_9$, or $R_{10}$, respectively, is not present;
(xix) $R_6$ is
  H,
  $C_{1-4}$alkyl,
  $C_{3-7}$cycloalkyl (e.g., cyclopentyl),
  aryl (e.g., phenyl),
  heteroaryl (e.g., pyridyl, for example, pyrid-4-yl),
  aryl$C_{1-4}$alkyl (e.g., benzyl),
  arylamino (e.g., phenylamino),
  heterarylamino,
  N,N-di$C_{1-4}$alkylamino,
  N,N-diarylamino,
  N-aryl-N-(aryl$C_{1-4}$alkyl)amino (e.g., N-phenyl-N-(1,1'-biphen-4-ylmethyl)amino), or
  —N($R_{18}$)($R_{19}$);
  wherein the aryl or heteroaryl is optionally substituted with one or more halo (e.g., F, Cl), hydroxy, $C_{1-6}$alkyl, $C_{1-6}$alkoxy, $C_{3-8}$cycloalkyl, for example, $R_6$ is 4-hydroxyphenyl or 4-fluorophenyl,
(xx) n=0 or 1;
(xxi) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy, (optionally hetero)aryl$C_{1-4}$alkyl or $R_{13}$ or $R_{14}$ can form a bridge with $R_2$ or $R_4$;
(xxii) $R_{15}$ is $C_{1-4}$alkyl, halo$C_{1-4}$alkyl, —OH or —O$C_{1-4}$alkyl (e.g., —OCH$_3$)
(xxiii) $R_{16}$ and $R_{17}$ are independently H or $C_{1-4}$alkyl;
(xxiv) $R_{18}$ and $R_{19}$ are independently
  H,
  $C_{1-4}$alky,
  $C_{3-8}$cycloalkyl,
  hetero$C_{3-8}$cycloalkyl,
  aryl (e.g., phenyl), or
  heteroaryl,
  wherein said aryl or heteroaryl is optionally substituted with one or more
    halo (e.g., fluorophenyl, e.g., 4-fluorophenyl),
    hydroxy (e.g., hydroxyphenyl, e.g., 4-hydroxyphenyl or 2-hydroxyphenyl),
    $C_{1-6}$alkyl,
    halo$C_{1-6}$alkyl,
    $C_{1-6}$alkoxy,
    aryl,
    heteroaryl, or
    $C_{3-8}$cycloalkyl;
(xxv) $R_{20}$ is H, $C_{1-4}$alkyl (e.g., methyl) or $C_{3-7}$cycloalkyl,
(xxvi) $R_{21}$ is $C_{1-6}$alkyl;
in free or salt form.

In yet another embodiment, the invention also provides a Compound of Formula IV:

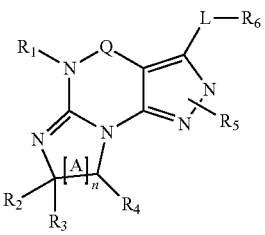

Formula IV wherein
(i) Q is C(=S), C(=N($R_{20}$)) or CH$_2$;
(ii) L is a single bond, —N(H)—, —CH$_2$—;
(iii) $R_1$ is H or $C_{1-4}$ alkyl (e.g., methyl or ethyl);
(iv) $R_4$ is H or $C_{1-6}$ alkyl (e.g., methyl, isopropyl) and $R_2$ and $R_3$ are, independently, H or $C_{1-6}$alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl), aryl, heteroaryl, (optionally hetero)arylalkoxy, or (optionally hetero)aryl$C_{1-6}$alkyl;
  or
  $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(v) $R_5$ is
  a) -D-E-F, wherein:
    D is $C_{1-4}$alkylene (e.g., methylene, ethylene or prop-2-yn-1-ylene);
    E is a single bond, $C_2$-4alkynylene (e.g., —C≡C—), arylene (e.g., phenylene) or heteroarylene (e.g., pyridylene);
    F is H, aryl (e.g., phenyl), heteroaryl (e.g., pyridyl, diazolyl, triazolyl, for example, pyrid-2-yl, imidazol-1-yl, 1,2,4-triazol-1-yl), halo (e.g., F, Br, Cl), halo$C_{1-4}$alkyl (e.g., trifluoromethyl), —C(O)—$R_{15}$, —N($R_{16}$)($R_{17}$), —S(O)$_2R_{21}$ or $C_{3-7}$cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
    wherein D, E and F are independently and optionally substituted with one or more:
      halo (e.g., F, Cl or Br),
      $C_{1-4}$alkyl (e.g., methyl),
      halo$C_{1-4}$alkyl (e.g., trifluoromethyl),
      for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-4}$alkyl (e.g., 5-trifluoromethylpyrid-2-yl) or $C_{1-4}$alkyl (e.g., 5-methylpyrid-2-yl),
      or F is aryl, e.g., phenyl, substituted with one or more halo (e.g., 4-fluorophenyl)
      or F is a $C_{3-7}$heterocycloalkyl (e.g., pyrrolidinyl) optionally substituted with a $C_{1-6}$alkyl (e.g., 1-methylpyrrolidin-3-yl);
    or
  b) a substituted heteroarylalkyl, e.g., substituted with haloalkyl;
  c) attached to one of the nitrogens on the pyrazolo portion of Formula IV and is a moiety of Formula A

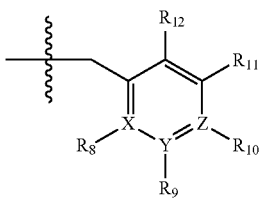

Formula A wherein X, Y and Z are, independently, N or C, and $R_8$, $R_9$, $R_{11}$ and $R_{12}$ are independently H or halogen (e.g., Cl or F), and $R_{10}$ is:
halogen,
$C_{1-4}$alkyl,
$C_{3-7}$cycloalkyl,
$C_{1-4}$haloalkyl (e.g., trifluoromethyl),
aryl (e.g., phenyl),
heteroaryl (e.g., pyridyl (for example pyrid-2-yl), or
thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
provided that when X, Y, or Z is nitrogen, $R_8$, $R_9$, or $R_{10}$, respectively, is not present;

(vi) $R_6$ is
H,
$C_{1-4}$alkyl,
$C_{3-7}$cycloalkyl (e.g., cyclopentyl),
aryl (e.g., phenyl),
heteroaryl (e.g., pyridyl, for example, pyrid-4-yl),
aryl$C_{1-4}$alkyl (e.g., benzyl),
arylamino (e.g., phenylamino),
heterarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$);
wherein the aryl or heteroaryl is optionally substituted with one or more halo (e.g., F, Cl), hydroxy or $C_{1-6}$alkoxy, for example, $R_6$ is 4-hydroxyphenyl or 4-fluorophenyl, (vii) n=0 or 1;
(viii) when n=1, A is —C($R_{13}R_{14}$)—, wherein $R_{13}$ and $R_{14}$, are, independently, H or $C_{1-4}$alkyl, aryl, heteroaryl, (optionally hetero)aryl$C_{1-4}$alkoxy or (optionally hetero)aryl$C_{1-4}$alkyl;
(ix) $R_{15}$ is $C_{1-4}$alkyl, halo$C_{1-4}$alkyl, —OH or —O$C_{1-4}$alkyl (e.g., —OCH$_3$)
(x) $R_{16}$ and $R_{17}$ are independently H or $C_{1-4}$alkyl;
(xi) $R_{18}$ and $R_{19}$ are independently H, $C_{1-4}$alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl)
(xii) $R_{20}$ is H, $C_{1-4}$alkyl (e.g., methyl) or $C_{3-7}$cycloalkyl,
(xiii) $R_{21}$ is $C_{1-6}$alkyl;
in free or salt form.

In still yet another embodiment, the invention provides that the PDE1 inhibitors for use in the methods of treatment and prophylaxis which are described herein are selected from any of the Applicant's own publications and applications: US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138, U.S. Ser. No. 12/064,599, U.S. Ser. No. 12/514,712, U.S. Ser. No. 12/517,945, U.S. Ser. No. 13/203,365, U.S. Ser. No. 13/319,807, U.S. Ser. No. 13/500,941 and U.S. Ser. No. 14/209,258, the entire contents of each of which are incorporated herein by reference in their entireties.

In yet another embodiment the invention provides that the PDE1 inhibitors for use in the methods of treatment and prophylaxis described herein are compounds of Formula V:

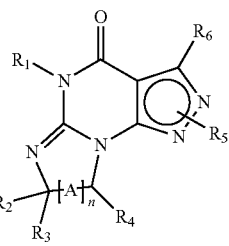

Formula V wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroarylalkyl, e.g., substituted with haloalkyl
or
$R_5$ is attached to one of the nitrogens on the pyrazolo portion of Formula V and is a moiety of Formula A

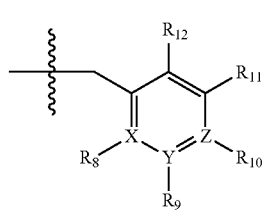

Formula A wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and
(iv) $R_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylakyl)amino (e.g., N-phenyl-N-(1,1'-biphen-4-ylmethyl)amino); and (v) n=0 or 1;
(vi) when n=1, A is —C(R₁₃R₁₄)—
wherein R₁₃ and R₁₄, are, independently, H or C₁₋₄ alkyl, aryl, heteroaryl, (optionally hetero)arylalkoxy or (optionally hetero)arylalkyl;

in free, salt or prodrug form, including its enantiomers, diastereoisomers and racemates.

In one embodiment the invention provides that the PDE1 inhibitors for use in the methods of treatment and prophylaxis described herein are compounds of Formula VI:

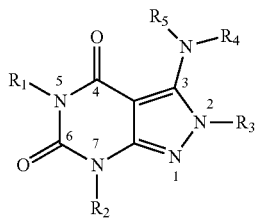

Formula VI wherein:
(i) R₁ is H or alkyl;
(ii) R₂ is H, alkyl, cycloalkyl, haloalkyl, alkylaminoalkyl, hydroxyalkyl, arylalkyl, heteroarylalkyl, or alkoxyarylalkyl;
(iii) R₃ is heteroarylmethyl or formula A

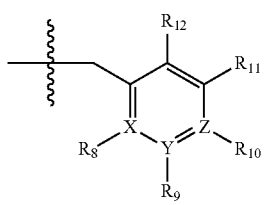

Formula A wherein X, Y and Z are, independently, N or C, and R₈, R₉, R₁₁ and R₁₂ are independently H or halogen; and R₁₀ is halogen, alkyl, cycloalkyl, haloalkyl, aryl, heteroaryl, alkyl sulfonyl, arylcarbonyl, heteroarylcarbonyl, alkoxycarbonyl, or aminocarbonyl;

(iv) R₄ is aryl or heteroaryl; and
(v) R₅ is H, alkyl, cycloalkyl, heteroaryl, aryl, p-benzylaryl;

provided that when X, Y or X is nitrogen, R₈, R₉ or R₁₀, respectively, is not present; wherein "alk" or "alkyl" refers to $C_{1-6}$ alkyl and "cycloalkyl" refers to $C_{3-6}$ cycloalkyl, in free, salt or physiologically hydrolysable and acceptable ester prodrug form.

In one embodiment the invention provides that the PDE1 inhibitors for use in the methods of treatment and prophylaxis described herein are compounds of Formula VII:

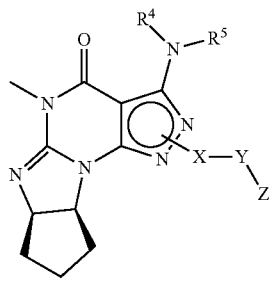

Formula VII (i) X is $C_{1-6}$alkylene (e.g., methylene, ethylene or prop-2-yn-1-ylene);
(ii) Y is a single bond, alkynylene (e.g., —C≡C—), arylene (e.g., phenylene) or heteroarylene (e.g., pyridylene);
(iii) Z is H, aryl (e.g., phenyl), heteroaryl (e.g., pyridyl, e.g., pyrid-2-yl), halo (e.g., F, Br, Cl), halo$C_{1-6}$alkyl (e.g., trifluoromethyl), —C(O)—R¹, —N(R²)(R³), or $C_{3-7}$cycloalkyl optionally containing at least one atom selected from a group consisting of N or O (e.g., cyclopentyl, cyclohexyl, tetrahydro-2H-pyran-4-yl, or morpholinyl);
(iv) R¹ is $C_{1-6}$alkyl, halo$C_{1-6}$alkyl, —OH or —O$C_{1-6}$alkyl (e.g., —OCH₃);
(v) R² and R³ are independently H or $C_{1-6}$alkyl;
(vi) R⁴ and R⁵ are independently H, $C_{1-6}$alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or $C_{1-6}$alkoxy;
(vii) wherein X, Y and Z are independently and optionally substituted with one or more halo (e.g., F, Cl or Br), $C_{1-6}$alkyl (e.g., methyl), halo$C_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-6}$alkyl (e.g., 5-trifluoromethylpyrid-2-yl) or $C_{1-6}$-alkyl (e.g., 5-methylpyrid-2-yl), or Z is aryl, e.g., phenyl, substituted with one or more halo (e.g., 4-fluorophenyl),
in free, salt or prodrug form.

In one embodiment the invention provides that the PDE1 inhibitors for use in the methods of treatment and prophylaxis described herein are compounds of Formula VIII:

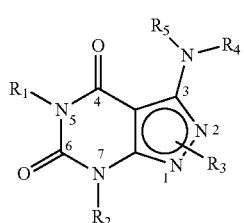

Formula VIII wherein
(i) R₁ is H or $C_{1-6}$alkyl;
(ii) R₂ is
H,
$C_{1-6}$alkyl,
$C_{3-8}$cycloalkyl optionally substituted with one or more amino,
$C_{3-8}$heterocycloalkyl optionally substituted with $C_{1-6}$alkyl, $C_{3-8}$cycloalkyl-$C_{1-6}$-alkyl,
$C_{1-6}$haloalkyl,
$C_{0-6}$alkylamino$C_{0-6}$alkyl,
hydroxy$C_{1-6}$alkyl,
aryl$C_{0-6}$alkyl,
heteroarylalkyl,
$C_{1-6}$alkoxyaryl$C_{1-6}$alkyl, or
-G-J wherein:
G is a single bond or, alkylene;
J is cycloalkyl or heterocycloalkyl optionally substituted with alkyl;
(iii) $R_3$ is
a) -D-E-F wherein
1. D is single bond, $C_{1-6}$alkylene or aryl$C_{1-6}$alkylene;
2. E is a $C_{1-6}$alkylene, arylene, $C_{1-6}$alkylarylene, amino$C_{1-6}$alkylene- or amino; and
3. F is hetero$C_{3-8}$cycloalkyl optionally substituted with $C_1$-6alkyl;
(iv) $R_4$ is aryl optionally substituted with one or more halo, hydroxyl or $C_{1-6}$alkoxy; heteroaryl; or hetero$C_{3-6}$cycloalkyl; and
(v) $R_5$ is H, $C_{1-6}$alkyl, $C_{3-8}$cycloalkyl, heteroaryl, aryl or p-benzylaryl; wherein "alk", "alkyl", "haloalkyl" or "alkoxy" refers to $C_{1-6}$ alkyl and "cycloalkyl" refers to $C_{3-8}$cycloalkyl;

in free or salt form.

In one embodiment the invention provides that the PDE1 inhibitors for use in the methods of treatment and prophylaxis described herein are compounds of Formula IX:

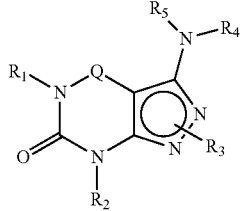

Formula IX wherein
(i) Q is —C(=S)—, —C(=N($R_6$))— or —C($R_{14}$)($R_{15}$)—;
(ii) $R_1$ is H or $C_{1-6}$alkyl (e.g., methyl or ethyl);
(iii) $R_2$ is
H,
$C_{1-6}$alkyl (e.g., isopropyl, isobutyl, 2-methylbutyl or 2,2-dimethylpropyl) wherein said alkyl group is optionally substituted with one or more halo (e.g., fluoro) or hydroxy (e.g., hydroxy$C_{1-6}$alkyl, for example 1-hydroxyprop-2-yl or 3-hydroxy-2-methylpropyl),
halo$C_{1-6}$alkyl (e.g., trifluoromethyl or 2,2,2-trifluoroethyl),
N($R_{14}$)($R_{15}$)—$C_{1-6}$alkyl (e.g., 2-(dimethylamino)ethyl or 2-aminopropyl),
aryl$C_{0-6}$alkyl (e.g., phenyl or benzyl), wherein said aryl is optionally substituted with one or more $C_{1-6}$alkoxy, for example, $C_{1-6}$alkoxyaryl$C_{0-6}$alkyl (e.g., 4-methoxybenzyl),
heteroaryl$C_{0-6}$alkyl (e.g., pyridinylmethyl), wherein said heteroaryl is optionally substituted with one or more $C_{1-6}$alkoxy (e.g., $C_{1-6}$alkoxyheteroaryl$C_{1-6}$alkyl);

-G-J wherein G is a single bond or $C_{1-6}$alkylene (e.g., methylene) and J is $C_{3-8}$cycloalkyl or hetero$C_{3-8}$cycloalkyl (e.g., oxetan-2-yl, pyrrolidin-3-yl, pyrrolidin-2-yl) wherein the cycloalkyl and heterocycloalkyl group are optionally substituted with one or more $C_{1-6}$alkyl or amino, for example,
—$C_{0-4}$alkyl-$C_{3-8}$cycloalkyl (e.g., —$C_{0-4}$alkyl-cyclopentyl, —$C_{0-4}$alkyl-cyclohexyl or —$C_{0-4}$alkyl-cyclopropyl), wherein said cycloalkyl is optionally substituted with one or more $C_{1-6}$alkyl or amino (for example, 2-aminocyclopentyl or 2-aminocyclohexyl),
—$C_{0-4}$alkyl-$C_{3-8}$heterocycloalkyl (e.g., —$C_{0-4}$alkyl-pyrrolidinyl, for example, —$C_{0-4}$alkylpyrrolidin-3-yl) wherein said heterocycloalkyl is optionally substituted with $C_{1-6}$alkyl (e.g., methyl), for example, 1-methylpyrrolidin-3-yl, 1-methyl-pyrrolindin-2-yl, 1-methyl-pyrrolindin-2-yl-methyl or 1-methyl-pyrrolindin-3-yl-methyl);
(iv) $R_3$ is
1) -D-E-F wherein:
D is a single bond, $C_{1-6}$alkylene (e.g., methylene), or aryl$C_{1-6}$alkylene (e.g., benzylene or —$CH_2C_6H_4$—);
E is
a single bond,
$C_{1-4}$alkylene (e.g., methylene, ethynylene, prop-2-yn-1-ylene),
$C_{0-4}$alkylarylene (e.g., phenylene or —$C_6H_4$—, -benzylene- or —$CH_2C_6H_4$—), wherein the arylene group is optionally substituted with halo (e.g., Cl or F),
heteroarylene (e.g., pyridinylene or pyrimidinylene),
amino$C_{1-6}$alkylene (e.g., —$CH_2$N(H)—),
amino (e.g., —N(H)—);
$C_{3-8}$cycloalkylene optionally containing one or more heteroatom selected from N or O (e.g., piperidinylene),
F is
H,
halo (e.g., F, Br, Cl),
$C_{1-6}$alkyl (e.g., isopropyl or isobutyl),
halo$C_{1-6}$alkyl (e.g., trifluoromethyl),
aryl (e.g., phenyl),
$C_{3-8}$cycloalkyl optionally containing one or more atom selected from a group consisting of N, S or O (e.g., cyclopentyl, cyclohexyl, piperidinyl, pyrrolidinyl, tetrahydro-2H-pyran-4-yl, or morpholinyl), and optionally substituted with one or more $C_{1-6}$alkyl (e.g., methyl or isopropyl), for example, 1-methylpyrrolidin-2-yl, pyrrolidin-1-yl, pyrrolidin-2-yl, piperidin-2-yl, 1-methyl-piperidin-2-yl, 1-ethylpiperidin-2-yl,
heteroaryl (e.g., pyridyl (for example, pyrid-2-yl), pyrimidinyl (for example, pyrimidin-2-yl), thiadiazolyl (for example, 1,2,3-thiadiazol-4-yl), diazolyl (e.g., pyrazolyl (for example, pyrazol-1-yl) or imidazolyl (for example, imidazol-1-yl, 4-methylimidazolyl, 1-methylimidazol-2-yl)), triazolyl (e.g., 1,2,4-triazol-1-yl), tetrazolyl (e.g., tetrazol-5-yl), alkyloxadiazolyl (e.g., 5-methyl-1,2,4-oxadiazol), wherein said heteroaryl is optionally substituted with one or more $C_{1-6}$alkyl, halo (e.g., fluoro) or halo$C_{1-6}$alkyl;

C$_{1-6}$alkoxy,
—O-haloC$_{1-6}$alkyl (e.g., —O—CF$_3$),
C$_{1-6}$alkylsulfonyl (for example, methylsulfonyl or —S(O)$_2$CH$_3$),
—C(O)—R$_{13}$, wherein R$_{13}$ is —N(R$_{14}$)(R$_{15}$), C$_{1-6}$alkyl (e.g., methyl), —OC$_{1-6}$alkyl (e.g., —OCH$_3$), haloC$_{1-6}$alkyl (trifluoromethyl), aryl (e.g., phenyl), or heteroaryl; —N(R$_{14}$)(R$_{15}$);
or
2) a substituted heteroarylC$_{1-6}$aklyl, e.g., substituted with haloC$_{1-6}$alkyl;
or
3) attached to one of the nitrogens on the pyrazolo portion of Formula I and is a moiety of Formula A

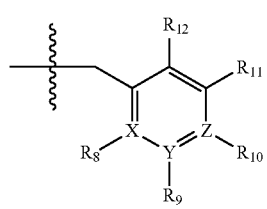

Formula A wherein:
X, Y and Z are, independently, N or C,
R$_8$, R$_9$, R$_{11}$ and R$_{12}$ are independently H or halogen (e.g., Cl or F); and
R$_{10}$ is
halogen (e.g., fluoro or chloro),
C$_{1-6}$alkyl,
C$_{3-8}$cycloalkyl,
heteroC$_{3-8}$cycloalkyl (e.g., pyrrolidinyl or piperidinyl), haloC$_{1-6}$alkyl (e.g., trifluoromethyl), aryl (e.g., phenyl) or heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkyloxadiazolyl (e.g., 5-methyl-1,2,4-oxadiazol), pyrazolyl (e.g., pyrazol-1-yl),
wherein said aryl, heteroaryl, cycloalkyl or heterocycloalkyl is optionally substituted with one or more C$_{1-6}$alkyl (e.g., methyl), halogen (e.g., chloro or fluoro), haloC$_{1-6}$alkyl (e.g., trifluoromethyl), hydroxy, carboxy, —SH, or an additional aryl or heteroaryl (e.g., biphenyl or pyridylphenyl),
C$_{1-6}$alkyl sulfonyl (e.g., methyl sulfonyl),
arylcarbonyl (e.g., benzoyl),
heteroarylcarbonyl,
C$_{1-6}$alkoxycarbonyl, (e.g., methoxycarbonyl),
Aminocarbonyl,
-N(R$_{14}$)(R$_{15}$);
preferably R$_{10}$ is phenyl, pyridyl, piperidinyl or pyrrolidinyl optionally substituted with the substituents previously defined, e.g. optionally substituted with halo or alkyl;
provided that when X, Y or X is nitrogen, R$_8$, R$_9$ or R$_{10}$, respectively, is not present;
(v) R$_4$ and R$_5$ are independently:
H,
C$_{1-6}$alkyl (e.g., methyl, isopropyl, isobutyl, n-propyl),
C$_{3-8}$cycloalkyl (e.g., cyclopentyl or cyclohexyl),
C$_{3-8}$heterocycloalkyl (e.g., pyrrolidinyl (for example pyrrolidin-3-yl or pyrrolidin-1-yl), piperidinyl (for example, piperidin-1-yl), morpholinyl),
—C$_{0-6}$alkylaryl (e.g., phenyl or benzyl) or
C$_{0-6}$alkylheteroaryl (e.g., pyrid-4-yl, pyrid-2-yl or pyrazol-3-yl)
wherein said aryl or heteroaryl is optionally substituted with one or more halo (e.g., 4-fluorophenyl), hydroxy (e.g., 4-hydroxyphenyl), C$_{1-6}$alkyl, C$_{1-6}$alkoxy or another aryl group (e.g., biphenyl-4-ylmethyl);
(vi) R$_6$ is H, C$_{1-6}$alkyl (e.g., methyl or ethyl) or C$_{3-8}$cycloalkyl;
(vii) R$_{14}$ and R$_{15}$ are independently H or C$_{1-6}$alkyl,
in free or salt form.

In one embodiment the invention provides that the PDE1 inhibitors for use in the methods of treatment and prophylaxis described herein are Formula X, e.g.:

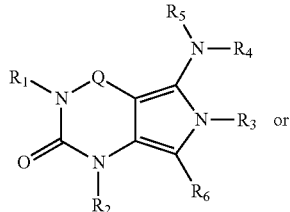

Formula XA

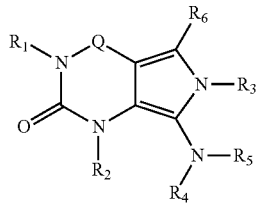

Formula XB

Formula X-A Formula X-B wherein
(i) Q is —C(=S)—, —C(=O)—, —C(=N(R$_7$))— or —C(R$_{14}$)(R$_{15}$)—;
(ii) R$_1$ is H or C$_{1-6}$alkyl (e.g., methyl or ethyl);
(iii) R$_2$ is H, C$_{1-6}$alkyl (e.g., isopropyl, isobutyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), for example, R$_2$ may be a trifluoromethyl or 2,2,2-trifluoroethyl, N(R$_{14}$)(R$_{15}$)— C$_{1-6}$alkyl (e.g., 2-(dimethylamino)ethyl or 2-aminopropyl), arylC$_{1-6}$alkyl (e.g., phenyl or benzyl), heteroaryl C$_{1-6}$alkyl (e.g., pyridinylmethyl), C$_{1-6}$alkoxyaryl-C$_{1-6}$alkyl (e.g., 4-methoxybenzyl); -G-J wherein:
G is a single bond or, alkylene (e.g., methylene); J is cycloalkyl or heterocycloalkyl (e.g., oxetan-2-yl, pyrolyin-3-yl, pyrolyin-2-yl) optionally substituted with one or more C$_{1-6}$alkyl (e.g., (1-methylpyrolidin-2-yl)), amino (e.g., —NH$_2$), for example, -G-J may be —C$_{0-4}$alkyl-C$_{3-8}$cycloalkyl (e.g., cyclopentyl, cyclohexyl or cyclopropylmethyl) optionally substituted with one or more C$_{1-6}$alkyl, amino (e.g., —NH$_2$), for example, 2-aminocyclopentyl or 2-aminocyclohexyl, wherein said cycloalkyl optionally contains one or more heteroatom selected from N and O (e.g., pyrrolidinyl, for example, pyrrolidin-3-yl or pyrrolidin-2-yl, 1-methyl-pyrrolindin-2-yl, 1-methyl-pyrrolindin-3-yl, 1-methyl-pyrrolindin-2-yl-methyl or 1-methyl-pyrrolindin-3-yl-methyl);

(iv) $R_3$ is

1) -D-E-F wherein:
D is a single bond, $C_{1-6}$alkylene (e.g., methylene), or arylalkylene
(e.g., p-benzylene or —$CH_2C_6H_4$—);
E is a single bond,
$C_{1-6}$alkylene (e.g., methylene) $C_{2-6}$alkynylene (e.g., ethynylene, prop-2-yn-1-ylene), ethynylene, prop-2-yn-1-ylene), -Co$_{-4}$alkylarylene (e.g., phenylene or —$C_6H_4$—, -benzylene- or —$CH_2C_6H_4$—), wherein the arylene group is optionally substituted with halo (e.g., Cl or F), heteroarylene (e.g., pyridinylene or pyrimidinylene), amino$C_{1-6}$alkylene (e.g., —$CH_2N$(H)—), amino (e.g., —N(H)—);
$C_{3-8}$cycloalkylene optionally containing one or more heteroatom selected from N or O (e.g., piperidinylene),
F is
H,
halo (e.g., F, Br, Cl), $C_{1-6}$alkyl (e.g., isopropyl or isobutyl), halo$C_{1-6}$alkyl (e.g., trifluoromethyl),
aryl (e.g., phenyl),
$C_{3-8}$cycloalkyl optionally containing at least one atom selected from a group consisting of N or O (e.g., cyclopentyl, N cyclohexyl, piperidinyl, pyrrolidinyl, tetrahydro-2H-pyran-4-yl, or morpholinyl), said cycloalkyl is optionally substituted with $C_{1-6}$alkyl (e.g., methyl or isopropyl), for example, 1-methylpyrrolidin-2-yl, pyrrolidin-1-yl, pyrrolidin-2-yl, piperidin-2-yl, 1-methyrpiperidin-2-yl, 1-ethylpiperidin-2-yl, heteroaryl optionally substituted with $C_{1-6}$alkyl, (e.g., pyridyl, (for example, pyrid-2-yl), pyrimidinyl (for example, pyrimidin-2-yl), thiadiazolyl (for example, 1,2,3-thiadiazol-4-yl), diazolyl (e.g., pyrazolyl (for example, pyrazol-1-yl) or imidazolyl (for example, imidazol-1-yl, 4-methylimidazolyl, 1-methylimidazol-2-yl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), wherein said heteroaryl is optionally substituted with halo (e.g., fluoro) or haloC$_{i-6}$alkyl, for example, 6-fluoropyrid-2-yl; amino (e.g., —$NH_2$), $C_{1-6}$alkoxy, —O-halo$C_{1-6}$alkyl (e.g., -0-$CF_3$), $C_{1-6}$alkylsulfonyl (for example, methylsulfonyl or —$S(O)_2CH_3$),
—C(O)—$R_3$,
—N($R_{14}$)($R_{15}$); or 2) a substituted heteroarylaklyl, e.g., substituted with haloalkyl; or 3) attached to the nitrogen on the pyrrolo portion of Formula I and is a moiety of Formula A

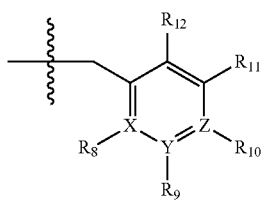

Formula A wherein X, Y and Z are, independently, N or C, and $R_8$, $R_9$, $R_{11}$ and $R_{12}$ are independently H or halogen (e.g., Cl or F); and $R_{10}$ is halogen, $C_{1-6}$alkyl,
$C_{1-6}$alkoxy (e.g., methoxy), $C_{3-8}$cycloalkyl, heteroC$_{3-8}$cycloalkyl (e.g., pyrrolidinyl) haloC$_{1-6}$alkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl (e.g., imidazolyl or pyrazolyl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), $C_{1-6}$alkyl sulfonyl (e.g., methyl sulfonyl), arylcarbonyl (e.g., benzoyl), heteroarylcarbonyl,
alkoxycarbonyl, (e.g., methoxycarbonyl), aminocarbonyl; wherein the aryl, heteroaryl, cycloalkyl or heterocycloalkyl is optionally substituted with one or more $C_{1-6}$alkyl (e.g., methyl), halogen (e.g., chloro or fluoro), haloC$_{1-6}$alkyl (e.g., trifluoromethyl), hydroxy, carboxy, —SH, or an additional aryl or heteroaryl (e.g., biphenyl or pyridylphenyl) preferably $R_{10}$ is phenyl or pyridyl, e.g., 2-pyridyl optionally substituted with the substituents previously defined;
provided that when X, Y or X is nitrogen, $R_8$, $R_9$ or $R_{10}$, respectively, is not present; (v) $R_4$ and $R_5$ are independently H, $C_{1-6}$alkyl (e.g., methyl, isopropyl),
$C_{3-8}$cycloalkyl (e.g., cyclopentyl), $C_{3-8}$heterocycloalkyl (e.g., pyrrolidin-3-yl), aryl (e.g., phenyl) or heteroaryl (e.g., pyrid-4-yl, pyrid-2-yl or pyrazol-3-yl) wherein said aryl or heteroaryl is optionally substituted with halo (e.g., 4-fluorophenyl), hydroxy (e.g., 4-hydroxyphenyl), $C_{1-6}$alkyl, $C_{1-6}$alkoxy or another aryl group (e.g., biphenyl-4-ylmethyl);
(vi) $R_6$ is H, $C_{1-6}$alkyl (e.g., methyl), hydroxy, $C_{1-6}$alkoxy, aryloxy, —N($R_{16}$)($R_{17}$), oxo (e.g., =0), or $C_{3-8}$Cycloalkyl;
(vii) $R_7$ is H, $C_{1-6}$alkyl (e.g., methyl) or $C_{3-8}$cycloalkyl wherein said cycloalkyl is optionally substituted with one or more oxo (e.g., 2,5-dioxopyrrolidin-1-yl);
(viii) $R_{13}$ is —N($R_{14}$)($R_{15}$), $C_{1-6}$alkyl (e.g., methyl), —OC$_{1-6}$alkyl (e.g., —$OCH_3$), haloC$_{1-6}$alkyl (trifluoromethyl), aryl (e.g., phenyl), or heteroaryl; and
(ix) $R_{14}$ and $R_{15}$ are independently H or $C_{1-6}$alkyl;
(x) $R_{16}$ and $R_{17}$ are independently H, $C_{1-6}$alkyl, aryl (e.g., phenyl), heteroaryl, wherein said aryl or heteroaryl is optionally substituted with halo (e.g., fluoro), $C_{1-6}$alkoxy (e.g., methoxy); in free or salt form.

In one embodiment the invention provides that the PDE1 inhibitors for use in the methods of treatment and prophylaxis described herein are Formula XI:

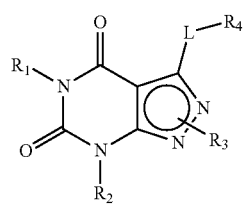

Formula XI wherein
(i) L is S, SO or $SO_2$;
(ii) $R_2$ is H or $C_{1-6}$alkyl (e.g., methyl or ethyl);
(iii) $R_2$ is
H,
$C_{1-6}$alkyl (e.g., isopropyl, isobutyl, neopentyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), —C$_{0-4}$alkyl-C$_{3-8}$cycloalkyl (e.g., cyclopentyl, cyclohexyl) optionally substituted with one or more amino (e.g., —NH$_2$, for example, 2-aminocyclopentyl or 2-aminocyclohexyl), wherein said cycloalkyl optionally contains one or more heteroatom selected from N and O and is optionally substituted with C$_{1-6}$alkyl (e.g., 1-methyl-pyrrolindin-2-yl, 1-methyl-pyrrolindin-3-yl, 1-methyl-pyrrolindin-2-yl-methyl or 1-methyl-pyrrolindin-3-yl-methyl), C$_{3-8}$heterocycloalkyl (e.g., pyrrolidinyl, for example, pyrrolidin-3-yl) optionally substituted with C$_{1-6}$alkyl (e.g., methyl), for example, 1-methylpyrrolidin-3-yl, C$_{3-8}$cycloalkyl-C$_{1-6}$alkyl (e.g., cyclopropylmethyl), haloC$_{1-6}$alkyl (e.g., trifluoromethyl, 2,2,2-trifluoroethyl), —N(R$_{14}$)(R$_{15}$)—C$_{1-6}$alkyl (e.g., 2-(dimethylamino) ethyl,2-aminopropyl), hydroxyC$_{1-6}$alkyl (e.g., (e.g., 3-hydroxy-2-methylpropyl, 1-hydroxyprop-2-yl), arylC$_{0-6}$alkyl (e.g., benzyl), heteroarylC$_{1-6}$alkyl (e.g., pyridinylmethyl), C$_{1-6}$alkoxyarylC$_{1-6}$alkyl (e.g., 4-methoxybenzyl); -G-J wherein: G is a single bond or, alkylene (e.g., methylene);

J is cycloalkyl or heterocycloalkyl (e.g., oxetan-2-yl, pyrolyin-3-yl, pyrolyin-2-yl) optionally substituted with C$_{1-6}$alkyl (e.g., (1-methylpyrolidin-2-yl));

(iv) R$_3$ is attached to one of the nitrogens on the pyrazolo portion of Formula I and is a moiety of Formula A

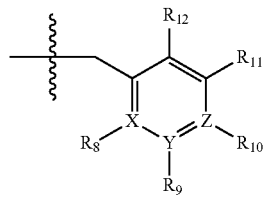

Formula A wherein X, Y and Z are, independently, N or C, and R$_8$, R$_9$, R$_{11}$ and R$_{12}$ are independently H or halogen (e.g., Cl or F); and R$_{10}$ is halogen, C$_{1-6}$alkyl, C$_{3-8}$cycloalkyl, heteroC$_{3-8}$cycloalkyl (e.g., pyrrolidinyl or piperidinyl) haloC$_{1-6}$alkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-15 yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-i-yl), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl, pyridyl, e.g., 2-pyridyl, piperidinyl, or pyrrolidinyl; wherein the aryl, heteroaryl cycloalkyl or heterocycloalkyl is optionally substituted with one or more halo (e.g., F or Cl), C$_{1-6}$alkly, C$_{1-6}$alkoxy, C$_{1-4}$haloalkyl (e.g., trifluoromethyl), and/or —SH, provided that when X, Y or X is nitrogen, R$_8$, R$_9$ or R$_{10}$, respectively, is not present;
(v) R$_4$ is H, C$_{1-6}$alkyl (e.g., methyl, isopropyl),
C$_{3-8}$cycloalkyl (e.g., cyclopentyl), C$_{3-8}$heterocycloalkyl (e.g., pyrrolidin-3-yl), aryl (e.g., phenyl) or heteroaryl (e.g., pyrid-4-yl, pyrid-2-yl or pyrazol-3-yl) wherein said aryl or heteroaryl is optionally substituted with halo (e.g., 4-fluorophenyl), hydroxy (e.g.,
4-hydroxyphenyl), C$_{1-6}$alkyl, C$_{1-6}$alkoxy or another aryl group (e.g., biphenyl-4-ylmethyl); (vi) R$_{14}$ and R$_{15}$ are independently H or C$_{1-6}$alkyl, in free or salt form.

The invention further provides the use of PDE1 inhibitors of any of the preceding formulae (e.g., Formula I, II, III, IV, V, VI, VII, VIII, IX, X, XI), wherein the compound is selected from any of the following:

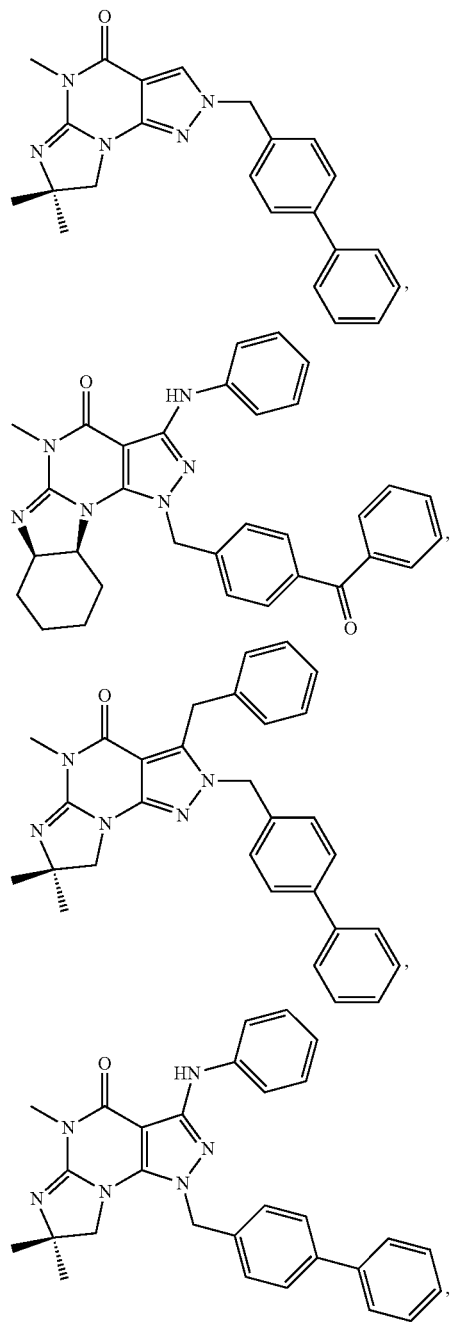

25
-continued
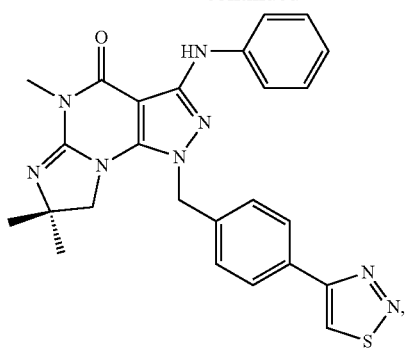
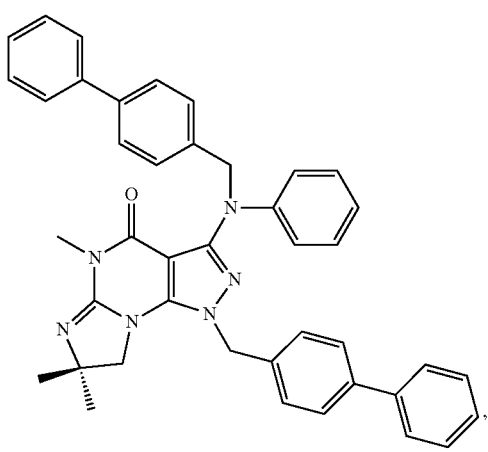
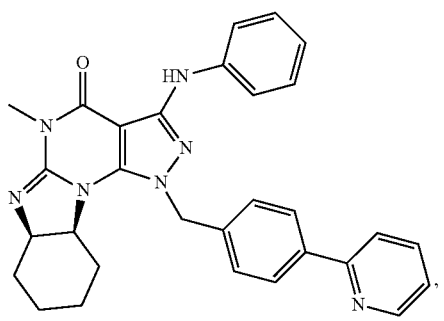
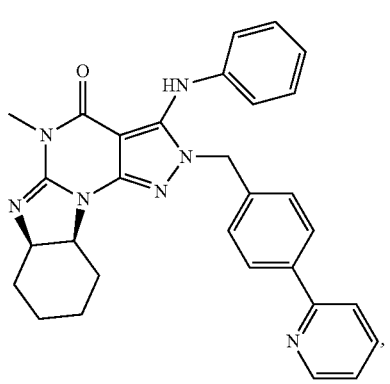
26
-continued
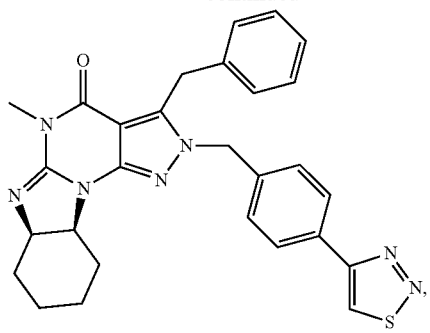
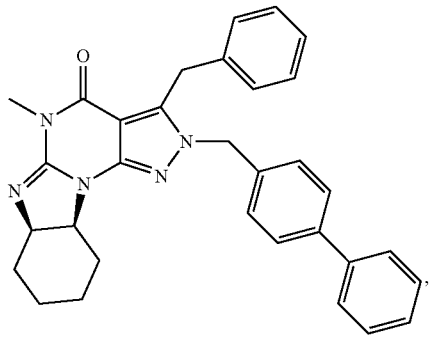
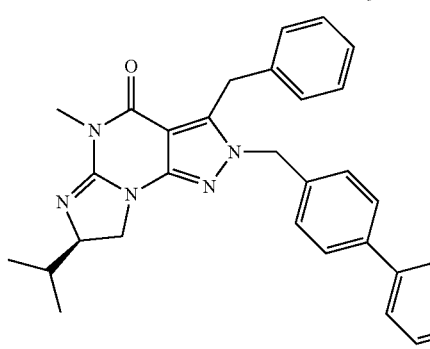
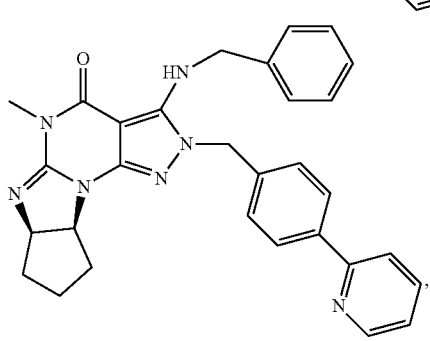
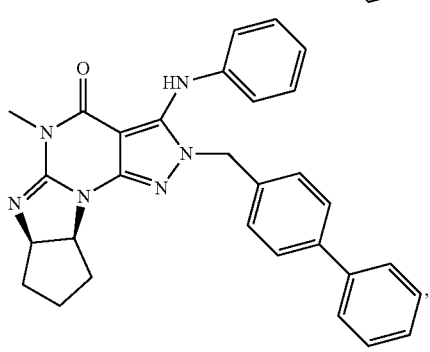

-continued
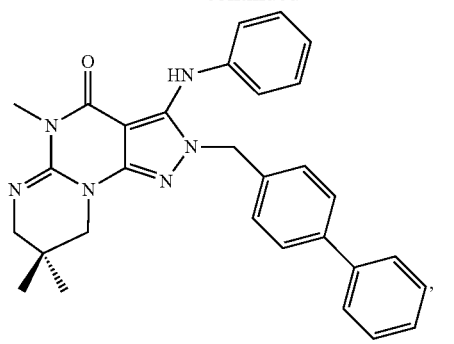
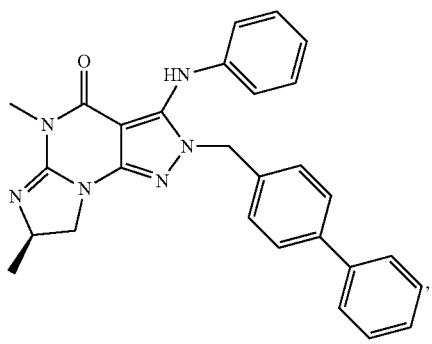
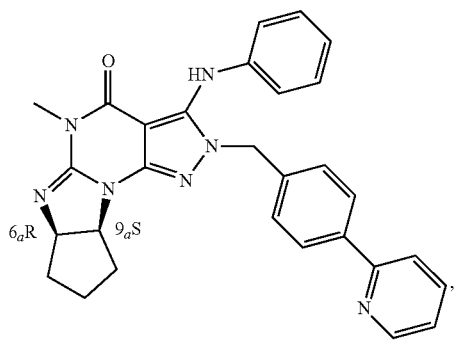
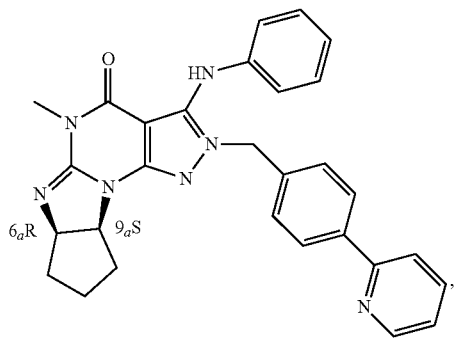
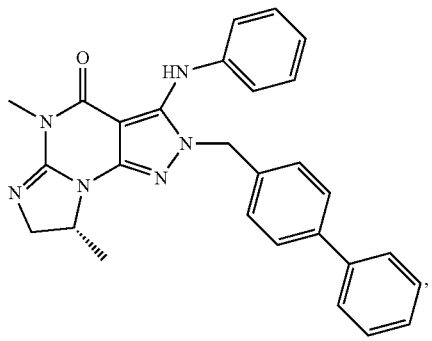
-continued
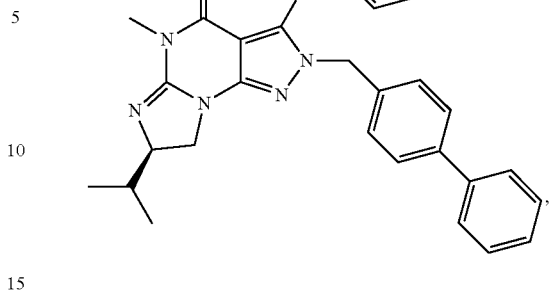
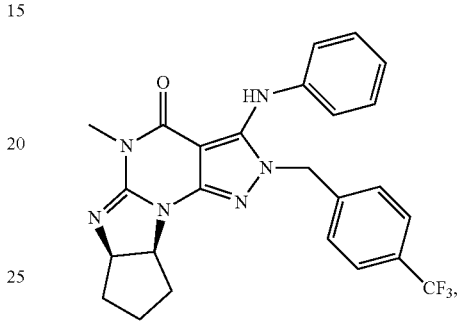
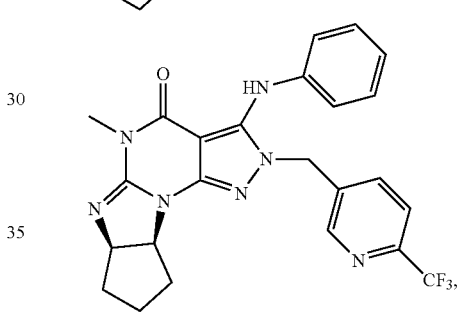
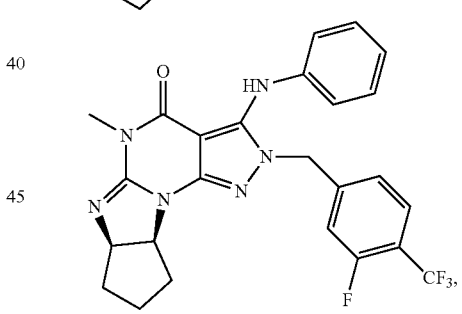
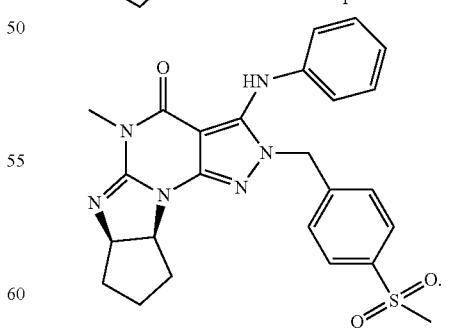
The invention further provides the use of PDE1 inhibitors of any of the preceding formulae (e.g., Formula I, II, III, IV, V, VI, VII, VIII, IX, X, XI), wherein the compound is selected from any of the following:

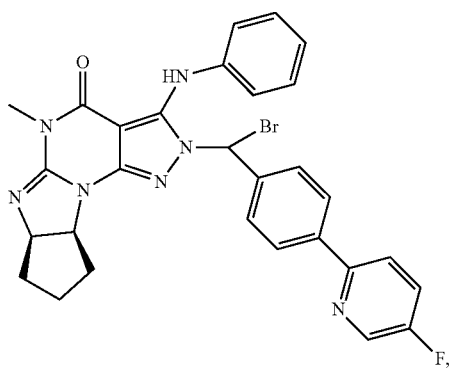
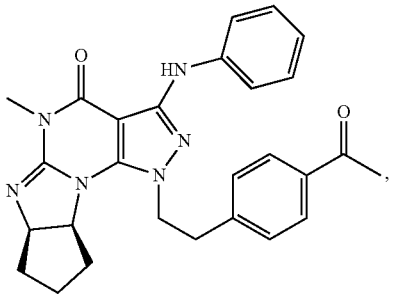
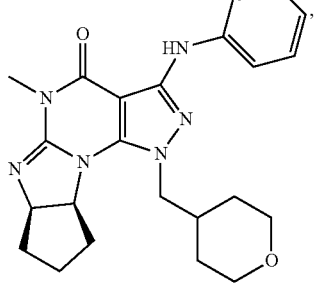
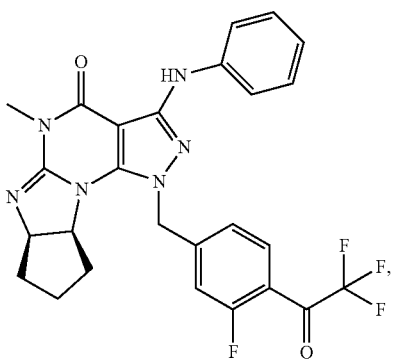
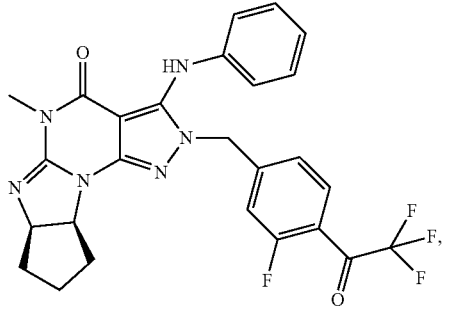
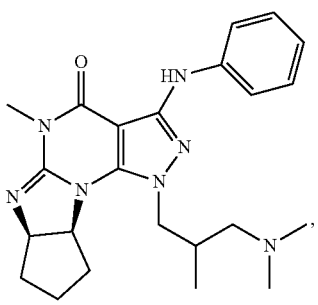
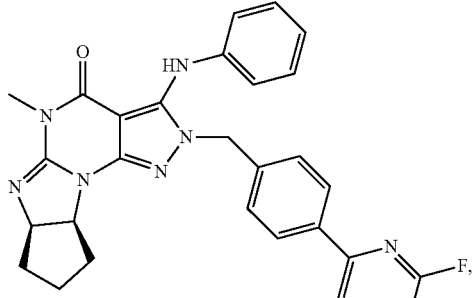
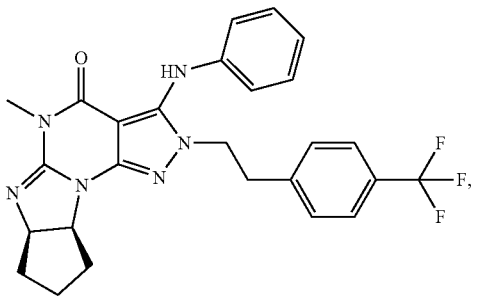
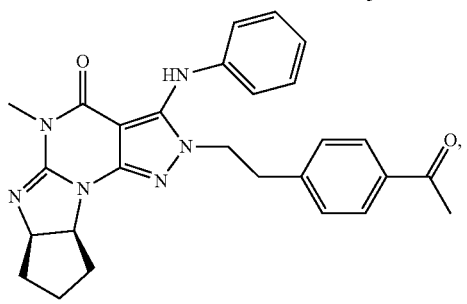
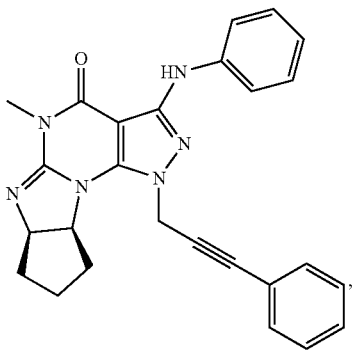

31
-continued
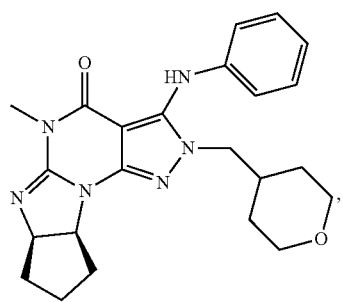
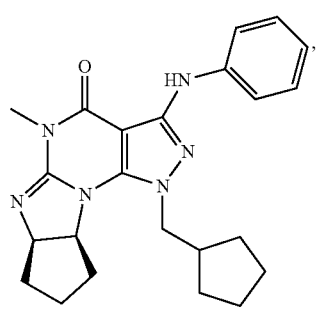
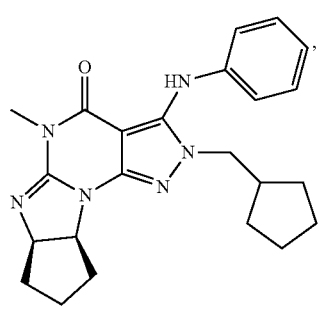
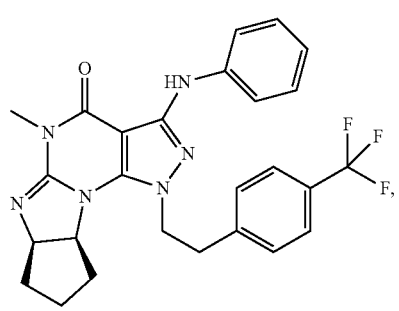
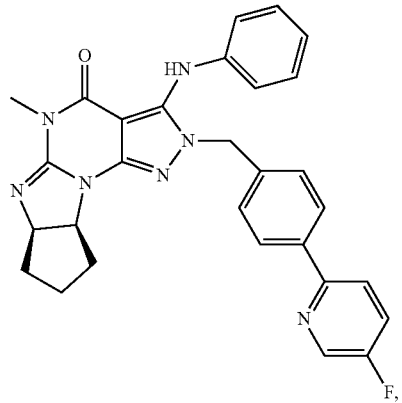
32
-continued
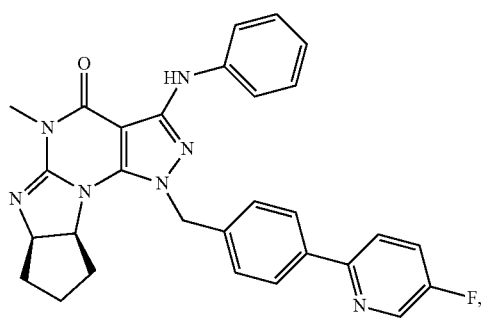
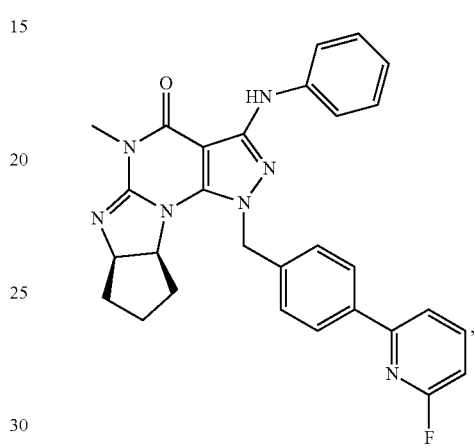
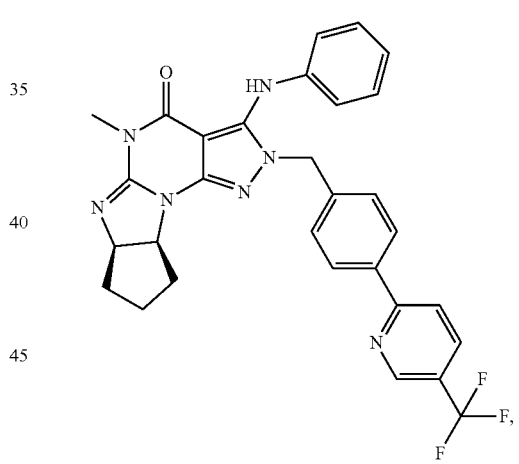
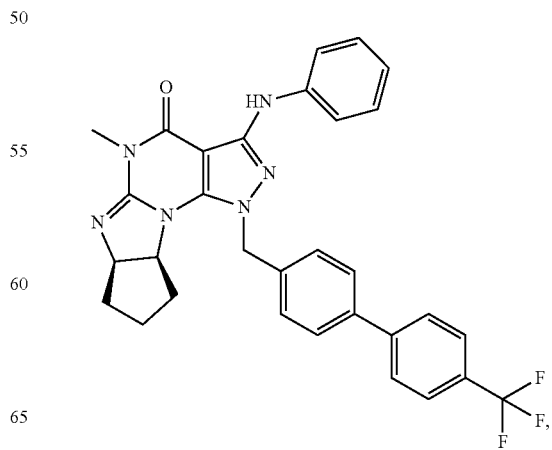

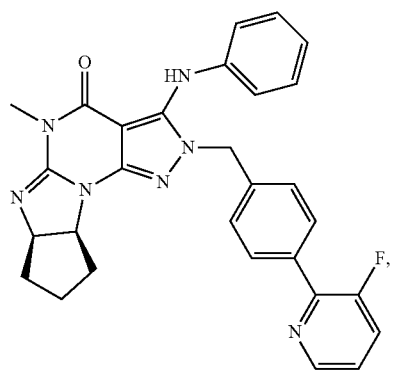
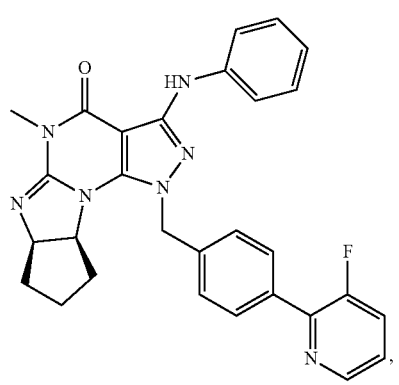
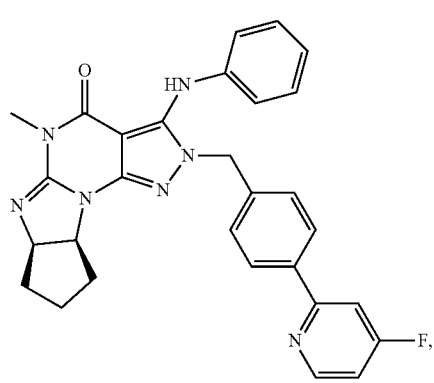
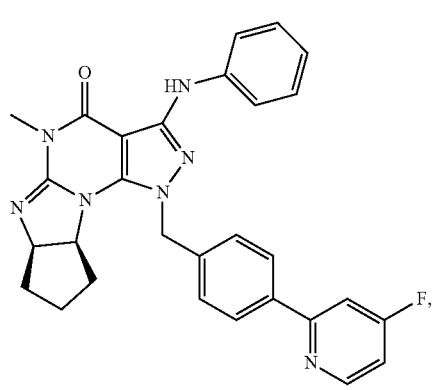
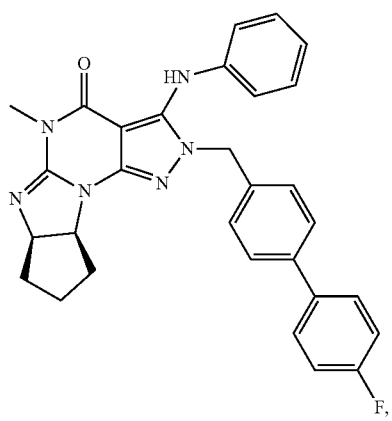
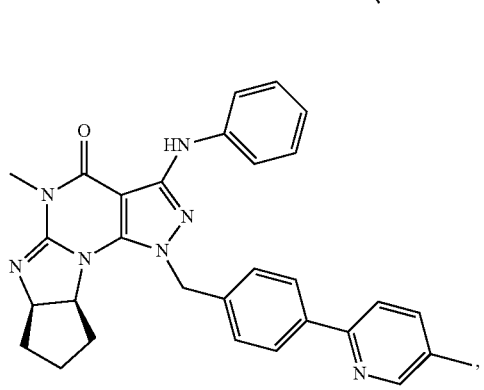

-continued
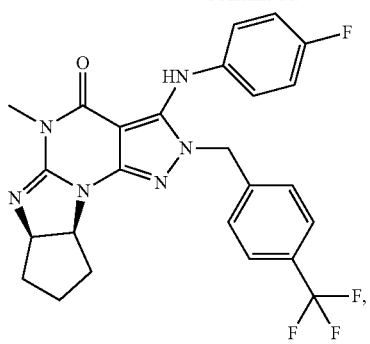
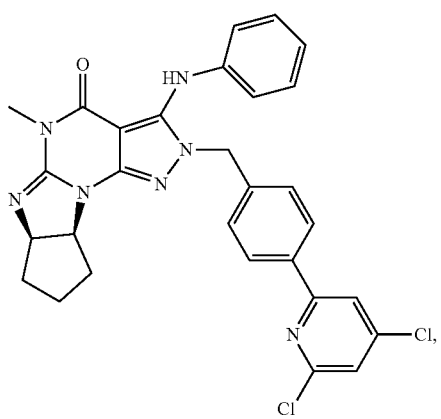
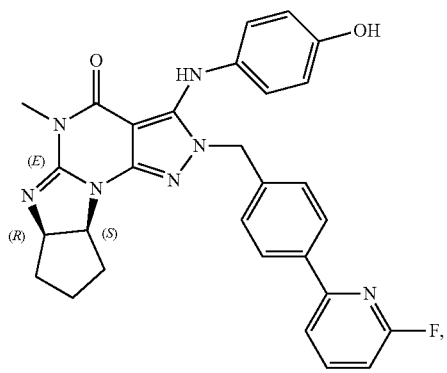
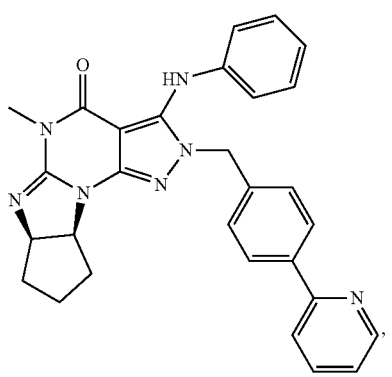
-continued
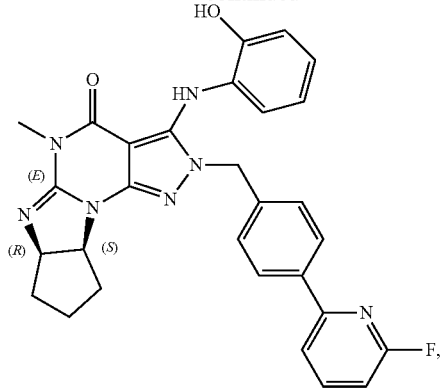
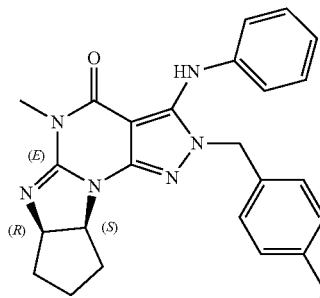
and
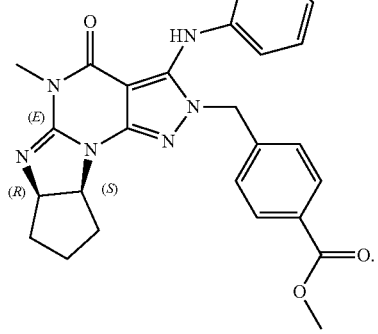
In yet another embodiment, the invention further provides the use of PDE1 inhibitors of any of the preceding formulae (e.g., Formula I, II, III, IV, V, VI, VII, VIII, IX, X, XI), wherein the compound is selected from any of the following:
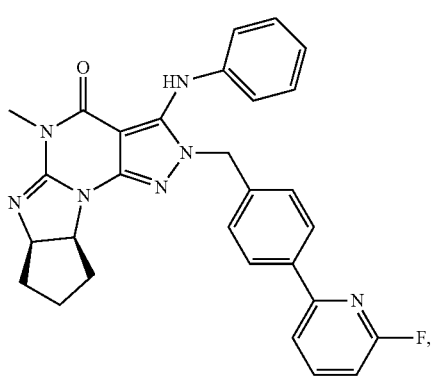

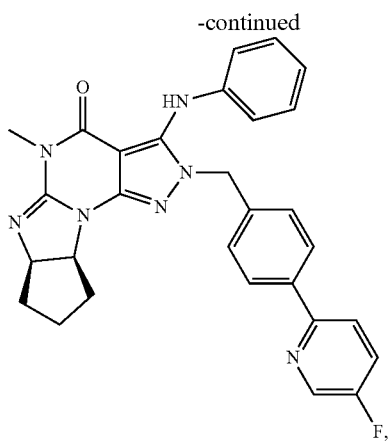
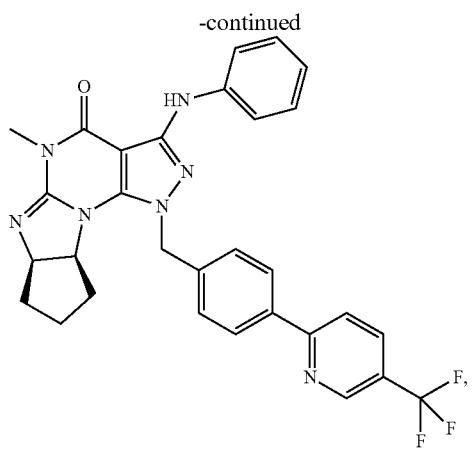
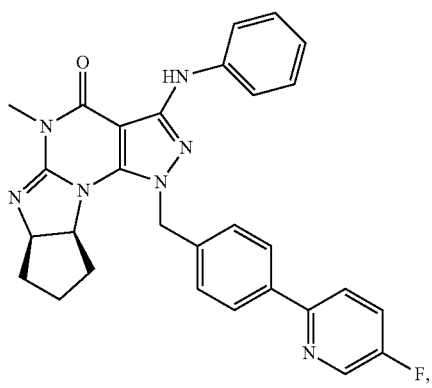
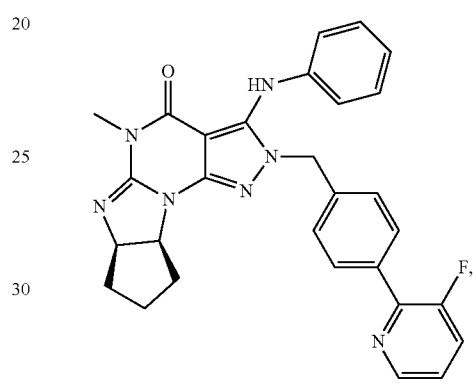
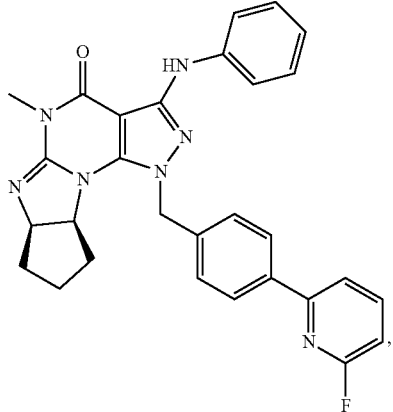
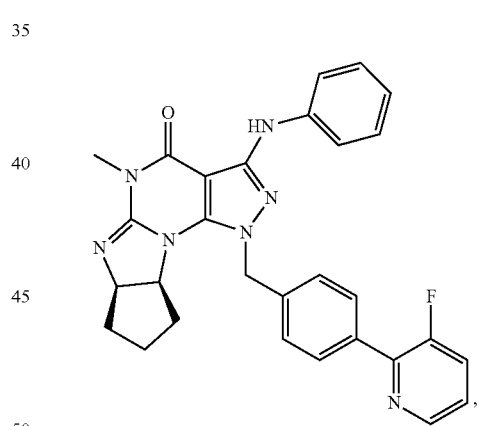
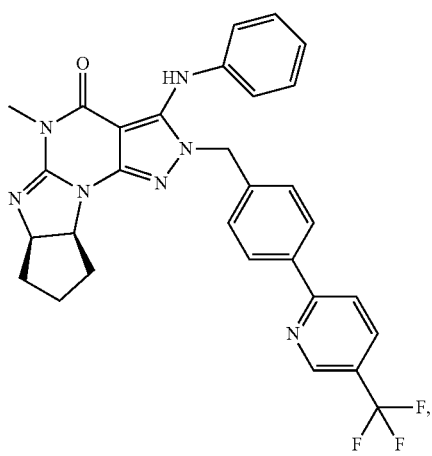
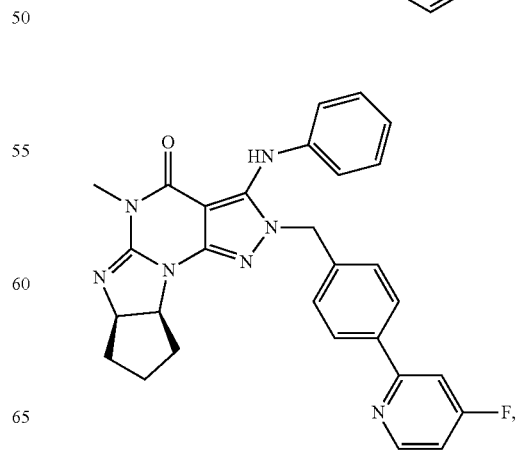

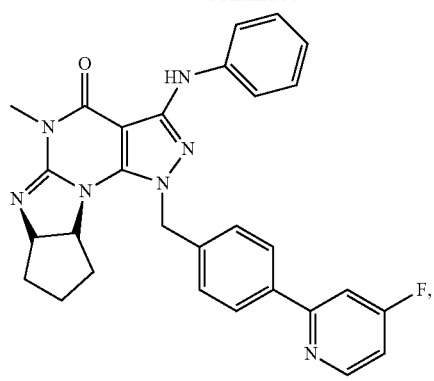
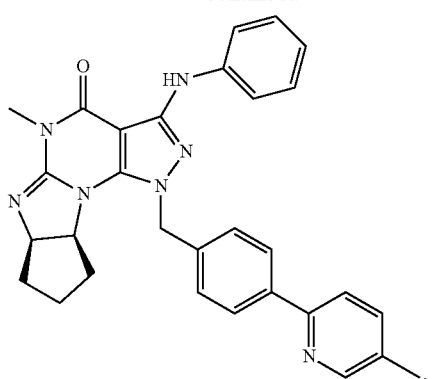
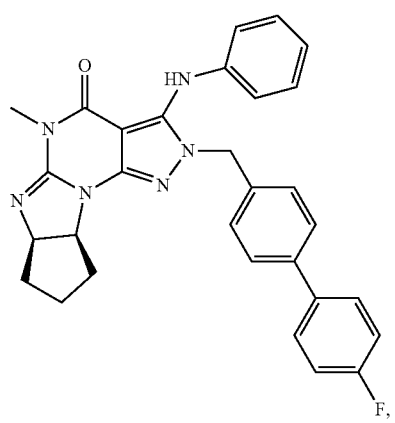
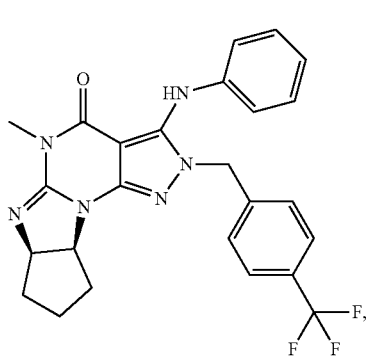
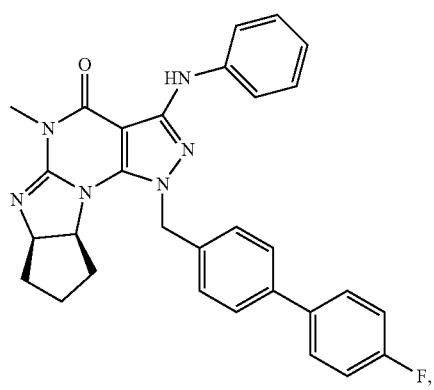
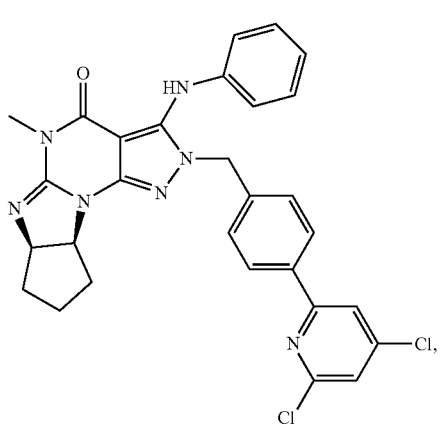
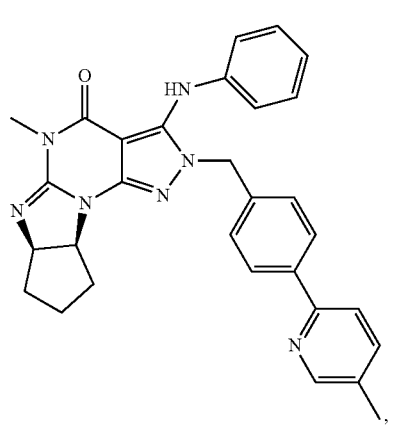
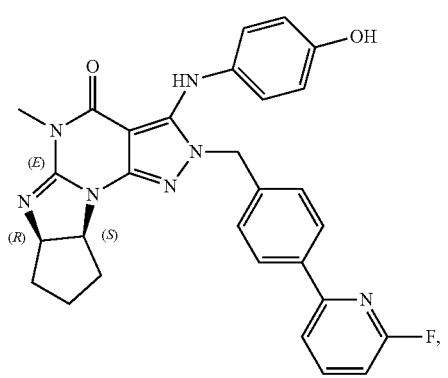

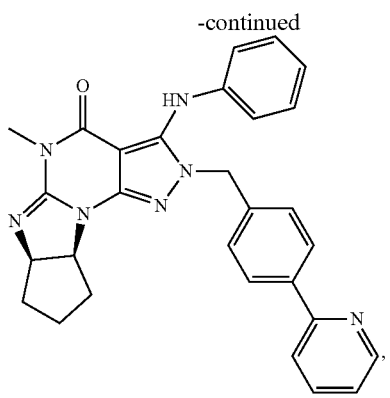
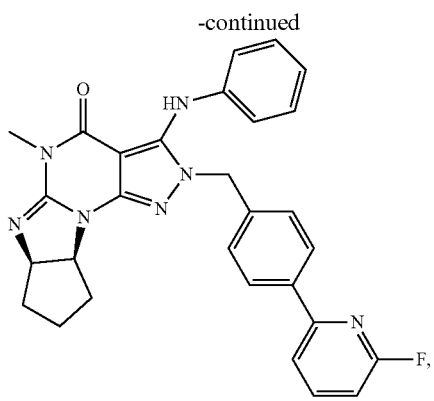
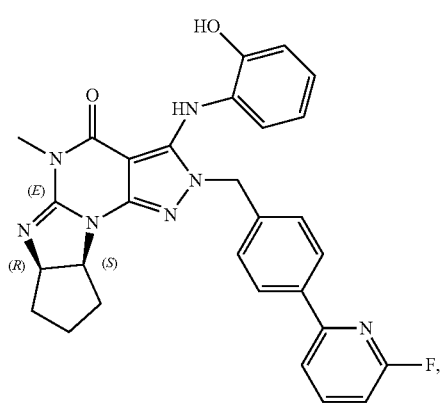
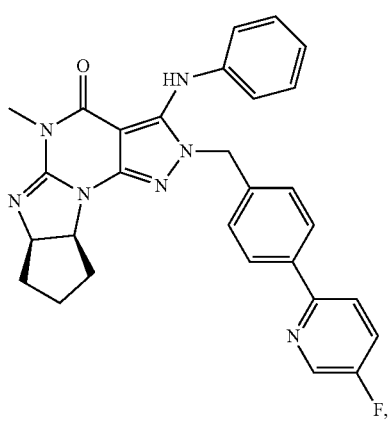
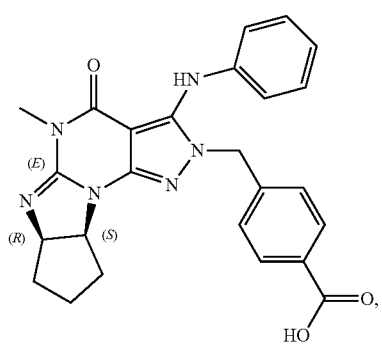
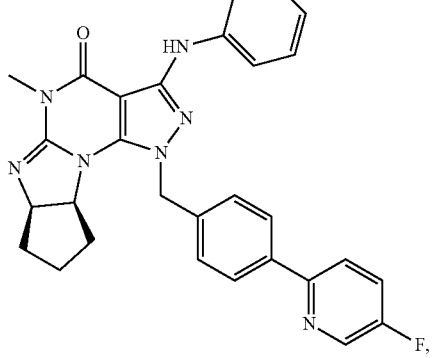
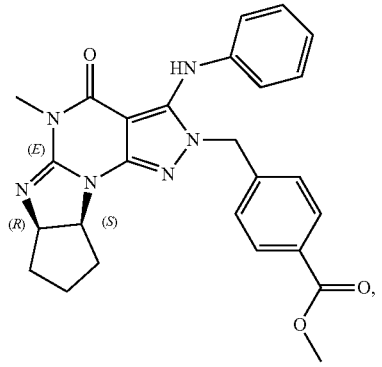
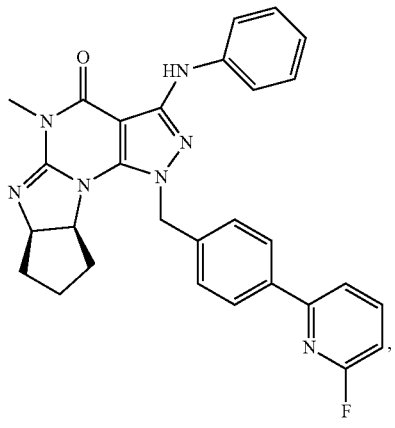

43
-continued
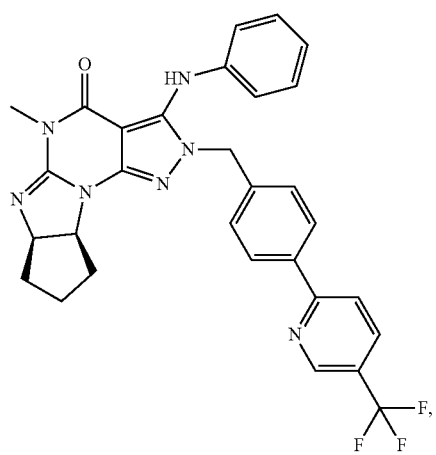
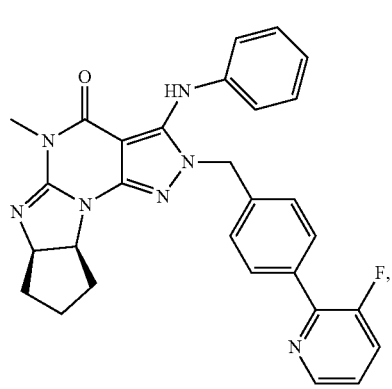
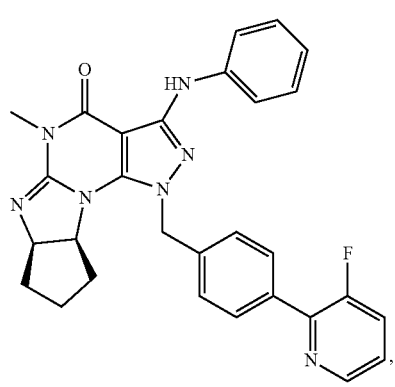
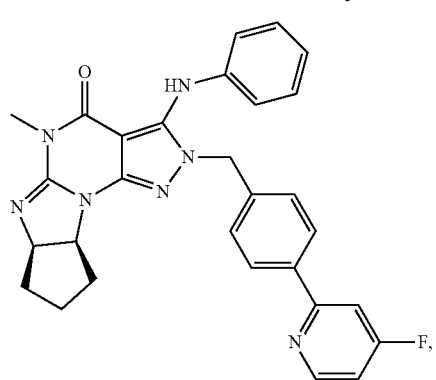
44
-continued
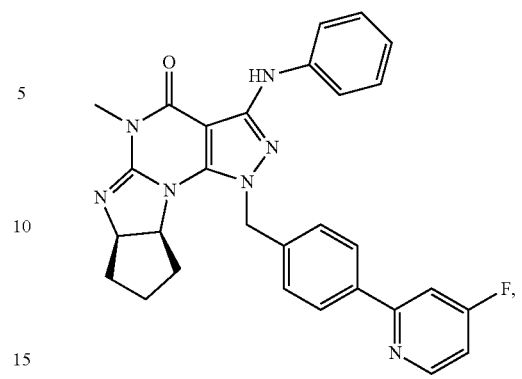
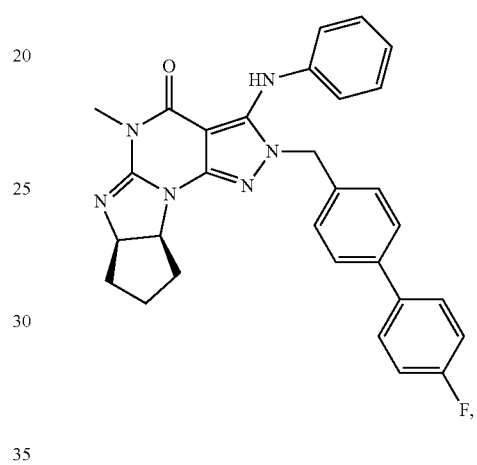
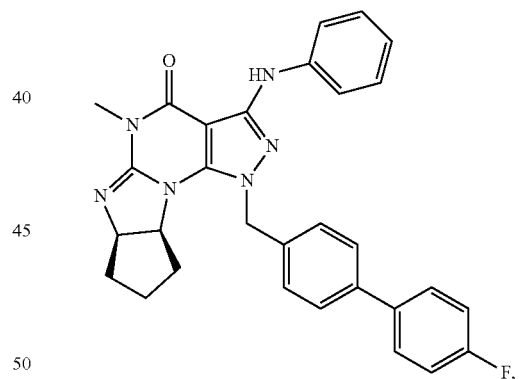
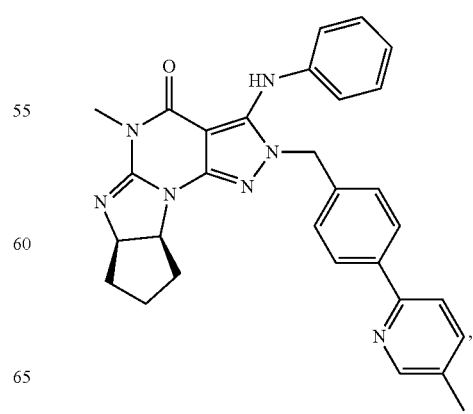

-continued
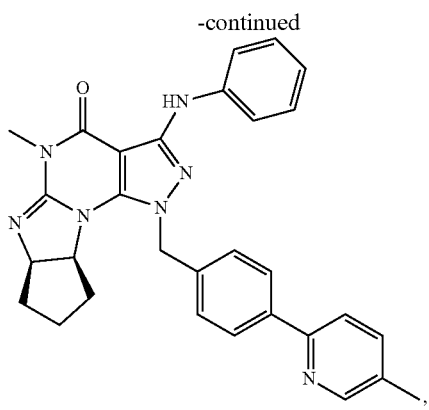
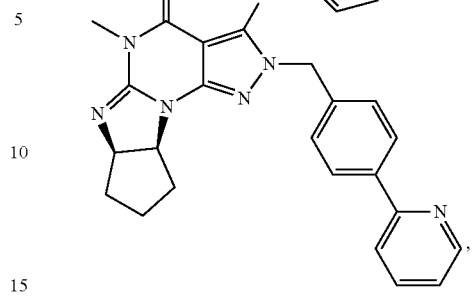
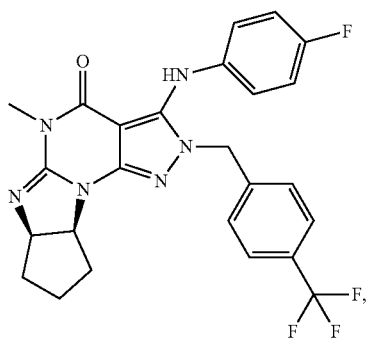
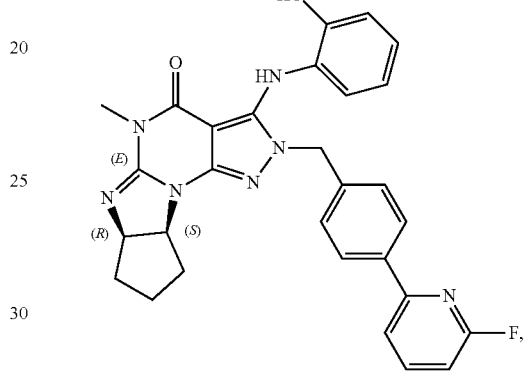
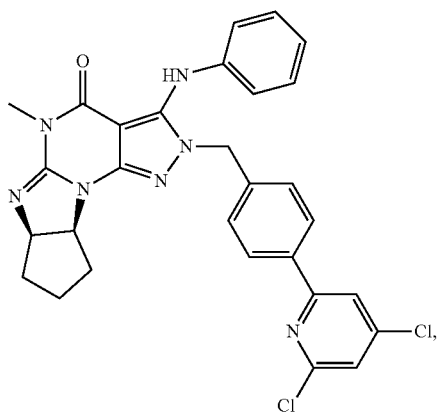
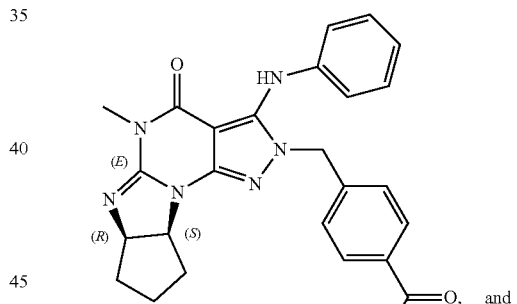
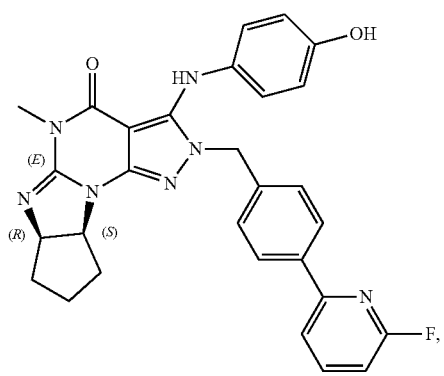
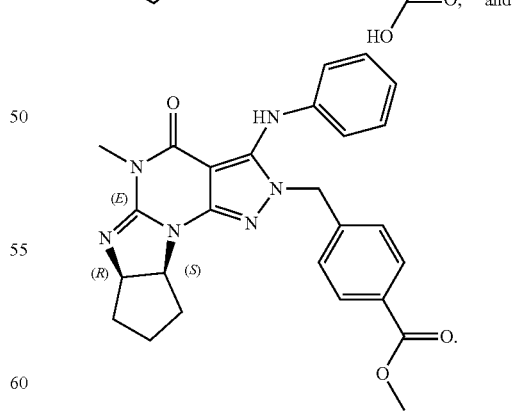
, and
In yet another embodiment, the invention further provides the use of PDE1 inhibitors of any of the preceding formulae (e.g., Formula I, II, III, IV, V, VI, VII, VIII, IX, X, XI), wherein the compound is selected from any of the following:

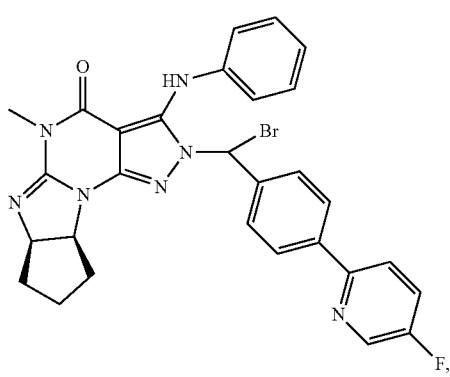
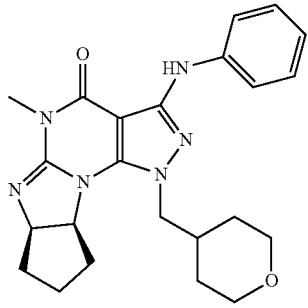
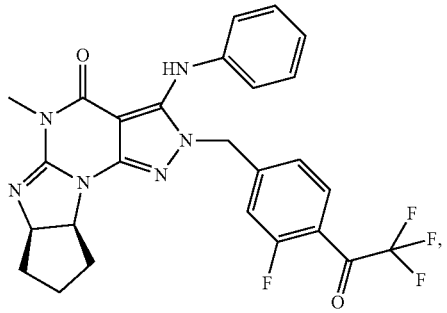
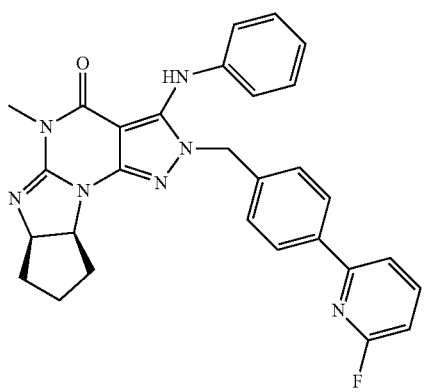
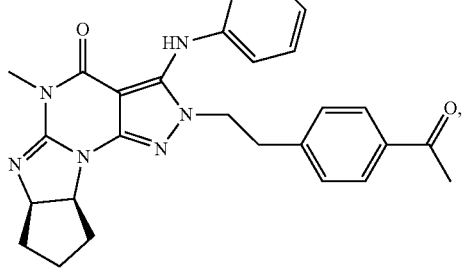
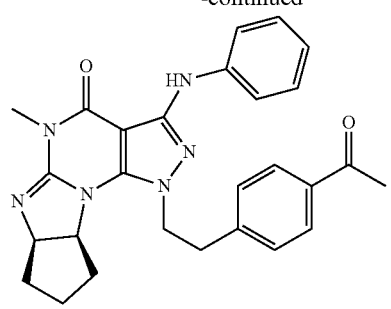
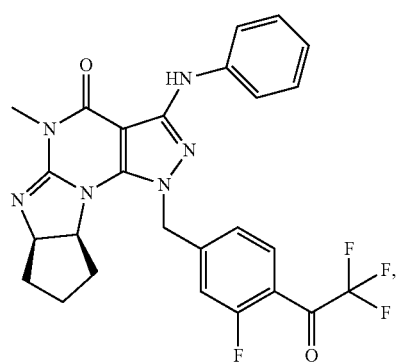
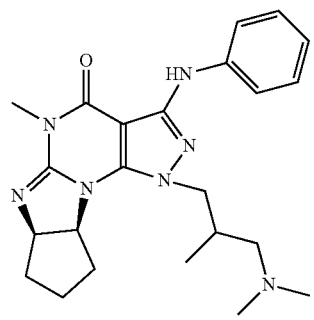
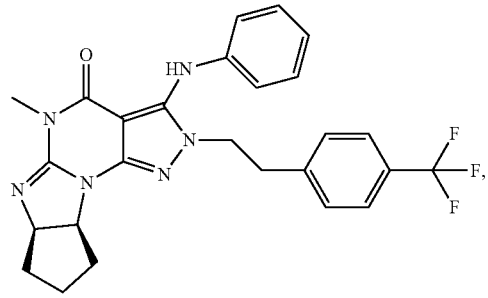
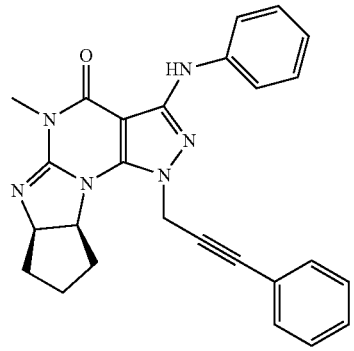

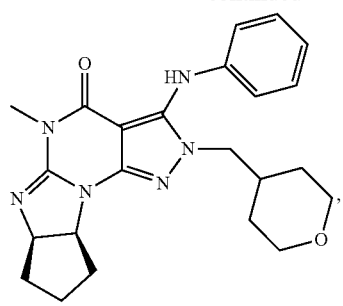
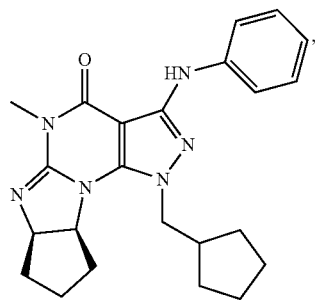
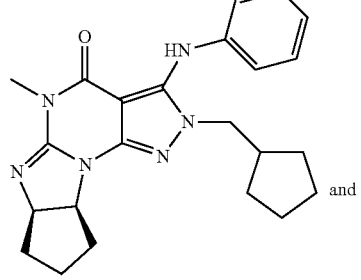 and
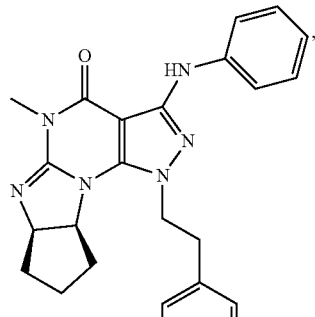
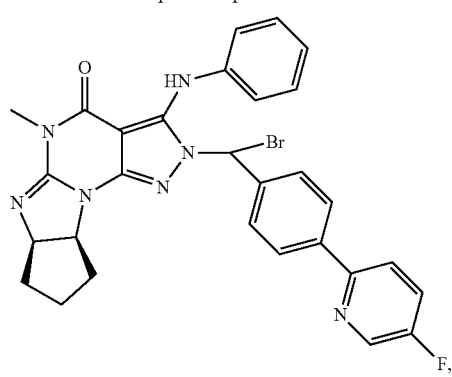
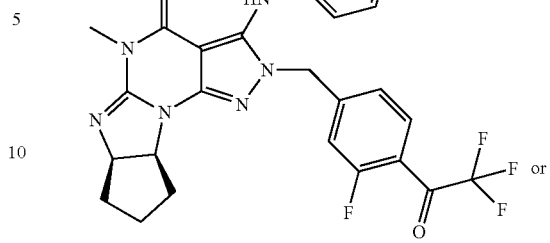 or
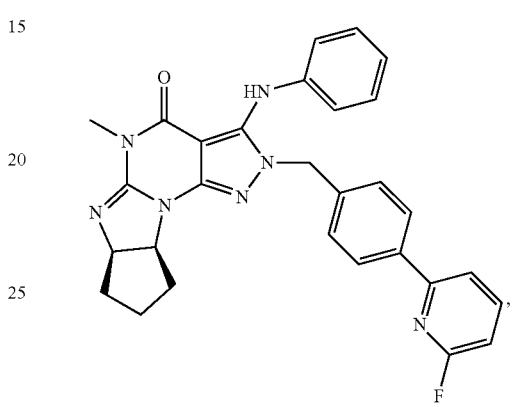
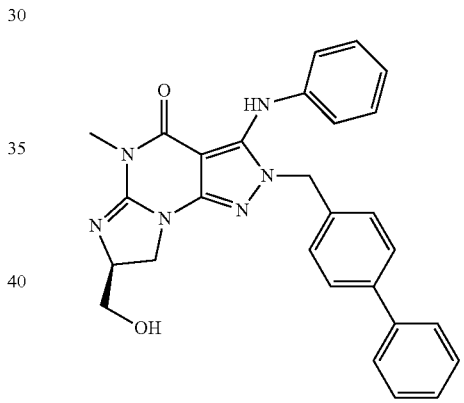
In a still further embodiment, the selective PDE1 inhibitors are selected from the following compounds which can be used either alone or in combination with another PDE1 inhibitor (e.g., any of Formula I-XI):
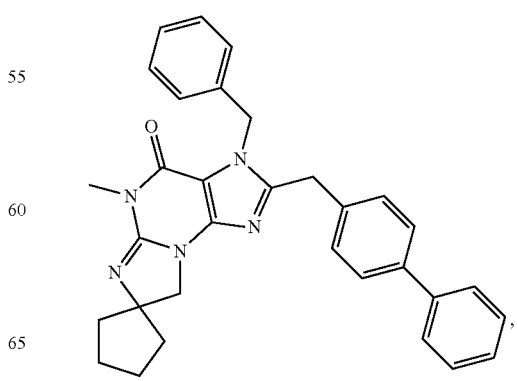

-continued

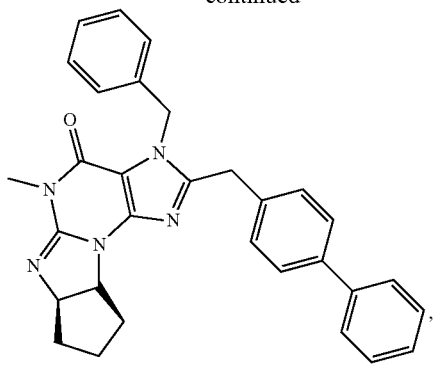

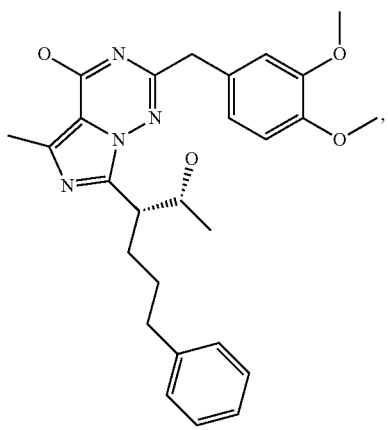

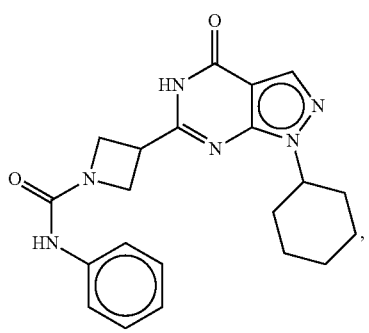

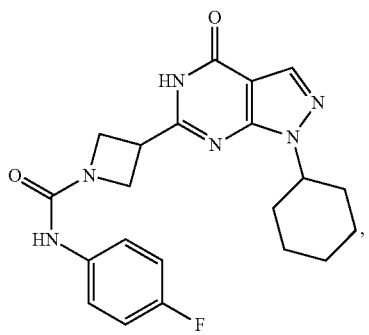

-continued

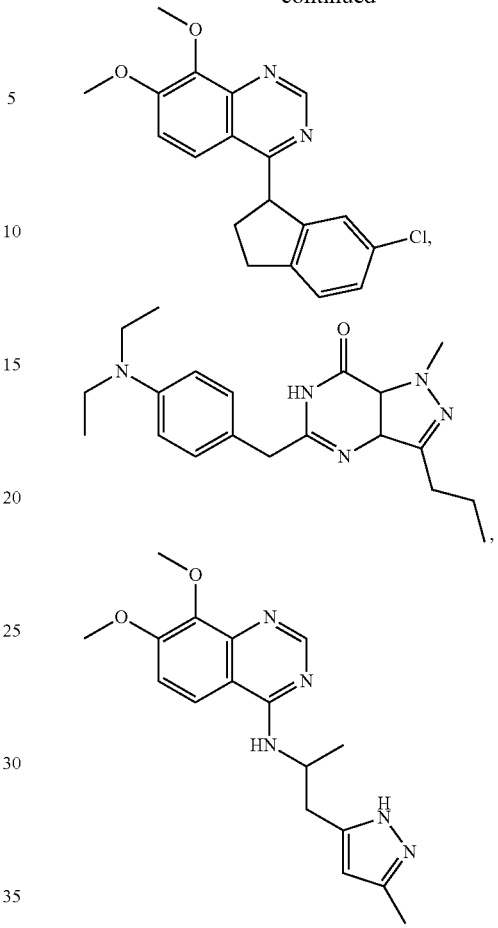

In one embodiment, selective PDE1 inhibitors of the any of the preceding formulae (e.g., Formula I, II, III, IV, V, VI, VII, VIII, IX, X, XI) are compounds that inhibit phosphodiesterase-mediated (e.g., PDE1-mediated, especially PDE1A or PDE1C-mediated) hydrolysis of cGMP, e.g., the preferred compounds have an $IC_{50}$ of less than 1 µM, preferably less than 500 nM, preferably less than 50 nM, and preferably less than 5 nM in an immobilized-metal affinity particle reagent PDE assay, in free or salt form.

If not otherwise specified or clear from context, the following terms herein have the following meanings:

(a) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

(b) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

(c) "Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

(d) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(e) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

(f) For ease of reference, the atoms on the pyrazolo-pyrimidine core of the Compounds of the Invention are numbered in accordance with the numbering depicted in Formula I, unless otherwise noted.

(g) Wherein E is phenylene, the numbering is as follows:

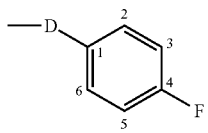

(h) It is intended that wherein the substituents end in "ene", for example, alkylene, phenylene or arylalkylene, said substitutents are intended to bridge or be connected to two other substituents. Therefore, methylene is intended to be —CH$_2$— and phenylene intended to be —C$_6$H$_4$— and arylalkylene is intended to be —C$_6$H$_4$—CH$_2$— or —CH$_2$—C$_6$H$_4$—.

(i) The Compounds of the Invention are intended to be numbered as follows:

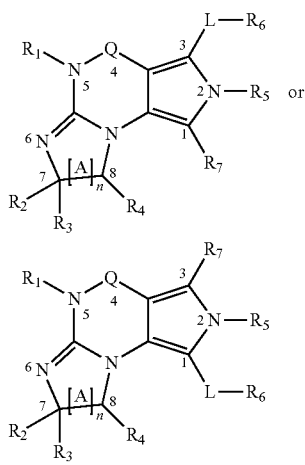

Compounds of the Invention, e.g., substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., Compounds of Formula I (Formula I-A and I-B), or a Compound of Formula II (e.g., II-A or II-B), may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention, encompassing any of the compounds disclosed herein, e.g., optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazolo[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4(5H)-thione or 7,8-dihydro-2H-imidazo[1,2-a]pyrazolo[4,3-e]pyrimidine-4(5H)-thione compounds, e.g., Compounds of Formula III, or Compound of Formula IV as described herein, may exist in free or salt form, e.g., as acid addition salts.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—C$_{1-4}$alkyl, can hydrolyze in the body to form physiologically hydrolysable alcohol (Compound-OH) on the one hand and acid on the other (e.g., HOC(O)—C$_{1-4}$alkyl). Alternatively, wherein the Compound of the Invention contains a carboxylic acid, for example, Compound-C(O)OH, the acid ester prodrug of such compound, Compound-C(O)O—C$_{1-4}$alkyl can hydrolyze to form Compound-C(O)OH and HO—C$_{1-4}$alkyl. As will be appreciated the term thus embraces conventional pharmaceutical prodrug forms.

In another embodiment, the invention further provides a pharmaceutical composition comprising a Compound of the Invention, in free or pharmaceutically acceptable salt form, in admixture with a pharmaceutically acceptable carrier.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

In another embodiment, the invention further provides a pharmaceutical composition comprising a Compound of the Invention, in free, pharmaceutically acceptable salt or prodrug form, in admixture with a pharmaceutically acceptable carrier.

Methods of Making Compounds of the Invention

The compounds of the Invention and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds.

Various starting materials and/or Compounds of the Invention may be prepared using methods described in US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138. All references cited herein are hereby incorporated by reference in their entirety.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-raradioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

Terms and Abbreviations:
BuLi=n-butyllithium
Bu$^t$OH=tert-butyl alcohol,
CAN=ammonium cerium (IV) nitrate,
DIPEA=diisopropylethylamine,
DMF=N,N-dimethylforamide,
DMSO=dimethyl sulfoxide,
$Et_2O$=diethyl ether,
EtOAc=ethyl acetate,
equiv.=equivalent(s),
h=hour(s),
HPLC=high performance liquid chromatography,
LDA=lithium diisopropylamide
MeOH=methanol,
NBS=N-bromosuccinimide
NCS=N-chlorosuccinimide
$NaHCO_3$=sodium bicarbonate,
$NH_4OH$=ammonium hydroxide,
$Pd_2(dba)_3$=tris[dibenzylideneacetone]dipalladium(0)
PMB=p-methoxybenzyl,
$POCl_3$=phosphorous oxychloride,
$SOCl_2$=thionyl chloride,
TFA=trifluoroacetic acid,
TFMSA=trifluoromethanesulfonic acid
THF=tetrahedrofuran.

Methods of Using Compounds of the Invention

In one embodiment the invention provides Method I, wherein Method I further comprises the prophylaxis and/or treatment of diseases, disorders, and injuries of the central nervous system, wherein the method comprises the administration of an effective amount of a PDE1 inhibitor (e.g., any compound of Formula I-XI) to modulate the level of intracellular cAMP.

For example, Method I also includes:

1.1. Method I, wherein the administration of the PDE1 inhibitor enhances the axonal growth or regeneration, and/or slows or reverses the loss of such cells in a neurodegenerative condition.
1.2. Any of preceding Method-I, et seq., wherein the CNS disease, disorder, or injury, refers to damage that directly or indirectly affects the normal functioning of the CNS.
1.3. Any of preceding Method-I, et seq., wherein the CNS disease, disorder, or injury can be a structural, physical, or mechanical impairment and may be caused by physical impact e.g.: crushing, compression, or stretching of nerve fibers.

1.4. Any of preceding Method-I, et seq., wherein the CNS disease, disorder, or injury is a spinal cord injury.

1.5. Method of 1.4, wherein the PDE1 inhibitor slows or arrests the progression of the spinal cord injury.

1.6. Any of preceding Method-I, et seq., wherein the PDE1 inhibitor slows or arrests axonal filament degradation.

1.7. Any of preceding Method-I, et seq. wherein the CNS disease, disorder, or injury relates to motor neuron trauma.

1.8. Any of preceding Method-I, et seq., wherein the disease, disorder, or injury is selected from the group consisting of: neurological traumas and injuries, surgery related trauma and/or injury, retinal injury and trauma, injury related to epilepsy, cord injury, spinal cord injury, brain injury, brain surgery, trauma related brain injury, trauma related to spinal cord injury, brain injury related to cancer treatment, spinal cord injury related to cancer treatment, brain injury related to infection, brain injury related to inflammation, spinal cord injury related to infection, spinal cord injury related to inflammation, brain injury related to environmental toxin, and spinal cord injury related to environmental toxin.

1.9. Any of preceding Method-I, et seq., wherein the CNS disease, disorder, or injury includes neuron or nerve fibers that may be destroyed by or degraded by an illness (e.g., Parkinson's Disease), a chemical imbalance, or a physiological malfunction such as anoxia (e.g., stroke), aneurysm, or reperfusion.

1.10. Any of preceding Method-I, et seq., wherein the CNS disease, disorder, or injury is a neurodegenerative disorder.

1.11. Method of 1.10, wherein the neurodegenerative disease, disorder, or injury is selected from the group consisting of: Alzheimer's disease, Multiple Sclerosis, Spinal Muscular Atrophy, Glaucoma, Frontotemporal dementia, Dementia with Lewy bodies, Corticobasal degeneration, Progressive supranuclear palsy, Prion disorders, Huntington's disease, Multiple system atrophy, Parkinson's disease, Amyotrophic lateral sclerosis, Hereditary spastic paraparesis, Spinocerebellar atrophies, Friedreich's ataxia, Amyloidoses, Metabolic (diabetes) related disorders, Toxin related disorders, chronic CNS inflammation, Charcot Marie Tooth disease, diabetic neuropathy, cancer chemotherapy (e.g., by vinca alkaloids and doxorubicin), brain damage associated with stroke and ischemia associated with stroke, and neurological disorders including, but not limited to, various peripheral neuropathic and neurological disorders related to neurodegeneration including, but not limited to: trigeminal neuralgia, glossopharyngeal neuralgia, Bell's palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by e.g., lead, acrylamides, gamma-diketones, carbon disulfide, dapsone, ticks, porphyria, and Gullain-Barre syndrome.

1.12. Any of preceding Method-I, et seq., wherein the CNS disease, disorder, or injury is a CNS lesion, a seizure (e.g., electroconvulsive seizure treatment; epileptic seizures), radiation, chemotherapy and/or stroke or other ischemic injury.

1.13. Any of preceding Method-I, et seq., wherein the administration of the PDE1 inhibitor is used to replenish, replace, and/or supplement neurons and/or glial cells.

1.14. Any of preceding Method-I, et seq., wherein the PDE1 inhibitor (e.g., a compound of any of Formula I-XI) is administered to a subject or a patient in need thereof.

1.15. Any of preceding Method-I, et seq., wherein the PDE1 inhibitor (e.g., a compound of any of Formula I-XI) elevates the level or expression of intracellular cAMP.

1.16. Any of preceding Method-I, et seq., wherein the PDE1 inhibitor (e.g., a compound of any of Formula I-XI) decreases the level or expression of intracellular cAMP.

1.17. Any of preceding Method-I, et seq., wherein the PDE1 inhibitor (e.g., a compound of any of Formula I-XI) modulates activity of PKA or PKG.

1.18. Any of preceding Method-I, et seq., wherein the PDE1inhibitor (e.g., a compound of any of Formula I-XI) increases the activity of PKA or PKG.

1.19. Any of preceding Method-I, et seq., wherein the administration of the PDE1 inhibitor (e.g., a compound of any of Formula I-XI) increases the level of both cAMP and cGMP.

1.20. Any of preceding Method-I, et seq., wherein the administration of the PDE1 inhibitor (e.g., a compound of any of Formula I-XI) elevates the level of intracellular cAMP, and wherein this increased level intracellular cAMP has neuroprotective and/or neuroregenerative properties.

1.21. Any of preceding Method-I, et seq., comprising administration of an effective amount of the PDE1 inhibitor (e.g., a compound of any of Formula I-XI) to a patient that suffers from a disease or disorder related to elevated (e.g., chronically elevated) intracellular calcium levels, and wherein the PDE1 inhibitor prevents a further rise in said calcium levels.

1.22. Any of preceding Method-I, et seq., wherein the PDE1 inhibitor is administered either alone or in combination with another active agent.

1.23. Any of preceding Method-I, et seq., wherein the disease, disorder, or injury is related to motor neurons, and wherein the motor neuron disease, disorder, or injury is Multiple Sclerosis.

1.24. Any of preceding Method-II, et seq., wherein the PDE1 inhibitor is administered in combination with another active agent in order to treat Multiple Sclerosis.

1.25. The method of 2.11, wherein the active agent is selected from the group consisting of: Interferon, Glatiramer acetate, Natalizumab, Gilenya® (fingolimod), Fampyra®, immunosuppresents, and corticoids.

In another embodiment the invention provides for Method II, wherein Method II comprises compositions and methods of treatment or prophylaxis of a peripheral nervous system (PNS) disease, disorder, or injury, wherein the method comprises administration of an effective amount of a PDE1 inhibitor to increase intracellular levels of cAMP.

For example, Method II also includes:

2.1. Method II, wherein the PNS disease, disorder, or injury, refers to damage that directly or indirectly affects the normal functioning of the CNS.

2.2. Any of preceding Method-II, et seq., wherein the PDE1 inhibitor is administered to a subject or a patient in need thereof.

2.3. Any of preceding Method-II, et seq., wherein the PDE1 inhibitor elevates the level or expression of intracellular cAMP.

2.4. Any of preceding Method-II, et seq., wherein the PDE1 inhibitor (e.g., directly or indirectly) modulates activity of PKA and/or PKG.

2.5. Any of preceding Method-II, et seq., wherein the PDE1 inhibitor (e.g., directly or indirectly) increases the activity of PKA and/or PKG.
2.6. Any of preceding Method-II, et seq., wherein the administration of the PDE1 inhibitor increases the level of cAMP and/or cGMP.
2.7. Any of preceding Method-II, et seq., wherein the administration of the PDE1 inhibitor elevates the level of intracellular cAMP, and wherein this increased level intracellular cAMP levels protects nerve fibers, regenerates nerve fibers, or promotes nerve fiber growth (e.g., axonal regeneration).
2.8. Any of preceding Method-II, et seq., comprising administration of an effective amount of the PDE1 inhibitor (e.g., a compound of any of Formula I-XI) to a patient that suffers from a disease or disorder related to elevated (e.g., chronically elevated) intracellular calcium levels.
2.9. Any of preceding Method-II, et seq., wherein the PDE1 inhibitor is administered either alone or in combination with another active agent.
2.10. The method of 2.9, wherein the active agent is selected from the IGF (e.g., IGF-1) or a steroid.
2.11. Any of preceding Method-II, et seq. wherein the PNS disease, disorder, or injury is selected from the group consisting of: neuropathy (e.g., peripheral neuropathy, autonomic neuropathy, and mononeuropathy), sciatica, carpal tunnel syndrome, polyneuropathy, diabetic neuropathy, postherpetic neuralgia, and thoracic outlet syndrome.

In another embodiment the invention provides for Method III, wherein Method III comprises compositions and methods to prevent a CNS disease or disorder in a subject that is at risk for developing said disease or disorder, wherein the method comprises:
1.) Obtaining a sample from the subject;
2.) Measuring the levels of intracellular calcium from the sample;
3.) Comparing the levels of intracellular calcium in the biological sample to a reference standard;
4.) Determining whether a patient is at risk for developing a CNS disease or disorder based upon the level of intracellular calcium compared to the reference standard;
5.) Administering a PDE1 inhibitor (e.g., a compound of any of Formula I-XI) to a subject based upon the subject's levels of intracellular calcium (e.g., administration of a PDE1 inhibitor to a subject because they have elevated intracellular calcium levels compared to the reference standard).

For example, Method III also includes:
3.1. Method III, wherein the sample is a biological sample.
3.2. Any of preceding Method-III, et seq., wherein the patient's intracellular calcium levels are measured using a chemical fluorescent probe.
3.3. Any of preceding Method-III, et seq., wherein the patient's intracellular calcium levels are elevated compared to a control (e.g., reference standard).
3.4. Any of preceding Method-III, et seq., wherein a PDE1 inhibitor is administered to a patient that is shown to have elevated intracellular calcium levels compared to a control (e.g., reference standard).
3.5. Any of preceding Method-III, et seq., wherein the administration of a PDE1 inhibitor slows or prevents the development of a CNS and/or PNS disease or disorder, wherein the CNS disease or disorder is one that correlates to elevated (e.g., chronically elevated) levels of intracellular calcium.
3.6. Any of preceding Method-III, et seq., wherein the administration of a PDE1 inhibitor decreases the likelihood that an individual will develop a CNS and/or PNS disease or disorder, wherein the CNS and/or PNS disease or disorder is one that correlates with elevated (e.g., chronically elevated) levels of intracellular calcium (e.g., any of the diseases, disorders or injuries listed in Method I, et seq., and Method II, et seq.).
3.7. Any of preceding Method-III, et seq., wherein the method optionally comprises measuring the patient's intracellular levels of cAMP or cGMP.
3.8. Any of preceding Method-III, et seq., wherein the PDE1 inhibitor is administered either alone or in combination with another active agent.
3.9. Any of preceding Method-III, et seq., wherein the PDE1 inhibitor is administered because a patient has low levels of cAMP and/or cGMP compared to a control subject.

The phrase "Compounds of the Invention" or "PDE1 inhibitors of the Invention" encompasses any and all of the compounds disclosed herewith, e.g., a Compound of Formula I, Formula II, Formula III, Formula IV, Formula V, Formula VI, Formula VII, Formula VIII, Formula IX, Formula X, or Formula XI, and any sub-formula (e.g., Formula II should be read as including both "Formula IIa and Formula IIb).

The words "treatment" and "treating" are to be understood accordingly as embracing prophylaxis and treatment or amelioration of symptoms of disease as well as treatment of the cause of the disease.

For methods of treatment, the word "therapeutically effective amount" as used herein refers to an amount of a drug (e.g., PDE1 inhibitor) sufficient to treat or ameliorate the pathological effects a CNS or PNS disease, disorder, or injury. For example, a therapeutically effective amount of a PDE1 inhibitor may be an amount sufficient to, e.g., increase intracellular levels of cAMP or cGMP, decrease intracellular levels of calcium, and/or increase neuroregeneration. Where relevant, a therapeutically effective amount may also be the amount of a PDE1 inhibitor necessary to slow or prevent the development of CNS or PNS disease or disorder.

The term "patient" or "subject" refers to human or nonhuman (i.e., animal) patient. In particular embodiment, the invention encompasses both human and nonhuman. In another embodiment, the invention encompasses nonhuman. In other embodiment, the term encompasses human.

The term "control subject" as used herein, refers to any human or nonhuman organism that does not have and/or is not suspected of having a disorder, syndrome, disease, condition and/or symptom. The term "reference standard" as used herein, refers to prior measurement and obtaining of results in a control population.

The term "biological sample" as used herein, may include any sample comprising biological material obtained from, e.g., an organism, body fluid, waste product, cell or part of a cell thereof, cell line, biopsy, tissue culture or other source containing a intracellular calcium, cAMP, or cGMP levels.

A "neurogenic agent" is defined as a chemical agent or reagent that can promote, stimulate, or otherwise increase the amount or degree or nature of neurogenesis in vivo or ex vivo or in vitro relative to the amount, degree, or nature of neurogenesis in the absence of the agent or reagent.

A "CNS injury" as used herein may include, e.g., damage to retinal ganglion cells, a traumatic brain injury, a stroke-related injury, a cerebral aneurysm-related injury, a spinal cord injury or trauma, including monoplegia, diplegia, paraplegia, hemiplegia and quadriplegia, a neuroproliferative disorder, or neuropathic pain syndrome A "PNS injury" as used herein may include, e.g., damage to the spinal or cranial nerves, wherein that damage may include a lesion or some acute or chronic trauma.

Compounds of the Invention, (e.g., any of Formula I, II, III, IV, V, VI, VII, VIII, IX, X, and XI) as hereinbefore described, in free or pharmaceutically acceptable salt form, may be used as a sole therapeutic agent, but may also be used in combination or for co-administration with other active agents.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

Example 1

Measurement of PDEIB Inhibition In Vitro Using IMAP Phosphodiesterase Assay Kit

Phosphodiesterase I B (PDEIB) is a calcium/calmodulin dependent phosphodiesterase enzyme that converts cyclic guanosine monophosphate (cGMP) to 5'-guanosine monophosphate (5'-GMP). PDEIB can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMPfluorescein-IMAP complex is large relative to cGMP-5 fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMPfluorescein, which, when bound to IMAP, yields a large increase in fluorescence polarization (Amp). Inhibition of phosphodiesterase, therefore, is detected as a decrease in Amp. Enzyme assay Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: The following phosphodiesterase enzymes may be used: 3',5'-cyclic-nucleotide specific bovine brain phosphodiesterase (Sigma, St. Louis, Mo.) (predominantly PDEIB) and recombinant full length human PDE1 A and PDE1B (r-hPDE1 A and r-hPDE1B respectively) which may be produced e.g., in HEK or SF9 cells by one skilled in the art. The PDE1 enzyme is reconstituted with 50% glycerol to 2.5 U/ml. One unit of enzyme will hydrolyze 1.0 μm of 3',5'-cAMP to 5'-AMP per min at pH 7.5 at 30° C. One part enzyme is added to 1999 parts reaction buffer (30 μM CaCl 2, 10 U/ml of calmodulin (Sigma P2277), 1 OmM Tris-HCl pH 7.2, 1 OmM MgCl2, 0.1% BSA, 0.05% NaN 3) to yield a final concentration of 1.25 mU/ml. 99 μM of diluted enzyme solution is added into each well in a flat bottom 96-well polystyrene plate to which 1 μM of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μM of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Amp).

A decrease in GMP concentration, measured as decreased Amp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus AmP, which allows $IC_{50}$ values to be estimated using nonlinear regression software (XLFit; IDBS, Cambridge, Mass.).

Example 2

A selective PDE1 inhibitor of the present invention demonstrates microsomal stability in human microsomal stability assays. The aforementioned selective PDE1 inhibitor demonstrates a K value less than 0.005, and demonstrates a half-life of T½ of about 275 minutes.

Example 3

A selective PDE1 inhibitor of the present invention demonstrates the ability to cross the blood-brain barrier. Following an injection of 10 mg/Kg in a suitable mouse model, the aforementioned selective PDE1 inhibitor is detectable at about 3 μM less than about 0.5 hours following the injection.

The invention claimed is:
1. A method for the treatment of a CNS disease, disorder, and/or injury, wherein the method comprises the administration of an effective amount of a PDE1 inhibitor to a subject in need thereof, wherein the administration of the PDE1 inhibitor modulates the subject's level of intracellular cAMP and is sufficient for axonal regeneration, wherein the PDE1 inhibitor is the following compound:

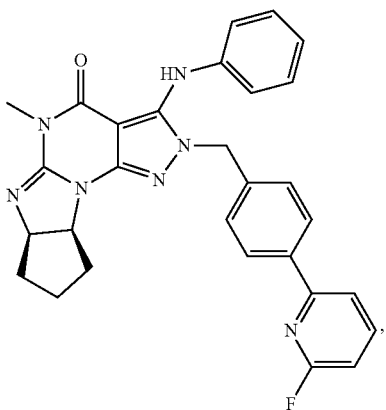 [SMILES: CN1C(=O)c2c(nn(Cc3ccc(-c4cccc(F)n4)cc3)c2Nc2ccccc2)N2C1=N[C@@H]1CCC[C@@H]12]

wherein the CNS disease, disorder, or injury is selected from the group consisting of: retinal injury or trauma, Alzheimer's disease, multiple sclerosis, glaucoma, frontotemporal dementia, dementia with Lewy bodies, corticobasal degeneration, progressive supranuclear palsy, prion disorders, Huntington's disease, multiple system atrophy, Parkinson's disease, amyotrophic lateral sclerosis, hereditary spastic paraparesis, spinocerebellar atrophies, friedreich's ataxia, amyloidoses, diabetic neuropathy, chronic CNS inflammation, and Charcot Marie tooth disease, in free or salt form.

2. A method of treatment of a PNS disease, disorder, or injury, wherein the method comprises administration of an effective amount of a PDE1 inhibitor to a subject in need thereof in order to increase the subject's intracellular levels of cAMP and is sufficient for axonal regeneration, wherein the PDE1 inhibitor is the following compound:

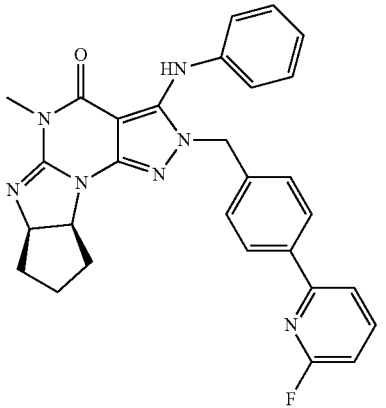 [SMILES: CN1C(=O)c2c(nn(Cc3ccc(-c4cccc(F)n4)cc3)c2Nc2ccccc2)N2C1=N[C@@H]1CCC[C@@H]12]

in free or salt form,
wherein the PNS disease, disorder, or injury is selected from the group consisting of: neuropathy, sciatica, carpal tunnel syndrome polyneuropathy, diabetic neuropathy, postherpetic neuralgia, and thoracic outlet syndrome.

3. A method of prophylaxis of the development of a CNS disease or disorder selected from the group consisting of: Alzheimer's disease, multiple sclerosis, glaucoma, frontotemporal dementia, dementia with Lewy bodies, corticobasal degeneration, progressive supranuclear palsy, prion disorders, Huntington's disease, multiple system atrophy, Parkinson's disease, amyotrophic lateral sclerosis, hereditary spastic paraparesis, spinocerebellar atrophies, friedreich's ataxia, amyloidoses, diabetic neuropathy, chronic CNS inflammation, and Charcot Marie tooth disease in a subject that is at risk for developing the CNS disease or disorder, wherein the method comprises:
1.) Obtaining a sample from the subject;
2.) Measuring the levels of intracellular calcium from the sample;
3.) Comparing the levels of intracellular calcium in the biological sample to a reference standard;
4.) Determining whether a patient is at risk for developing the CNS disease or disorder based upon the level of intracellular calcium compared to the reference standard;
5.) Administering a PDE1 inhibitor to a subject based upon the subject's levels of intracellular calcium put them at risk for the development of the CNS disease or disorder.

4. The method of claim 1, wherein a PDE1 inhibitor is administered to a patient that is shown to have elevated intracellular calcium levels compared to a control subject.

5. A method for enhancing axonal growth or regeneration, and/or slowing or reversing the loss of such cells in a neurodegenerative condition, the method comprising administering an effective amount of a PDE1 inhibitor to a patient in need thereof, wherein the PDE1 inhibitor is the following, compound:

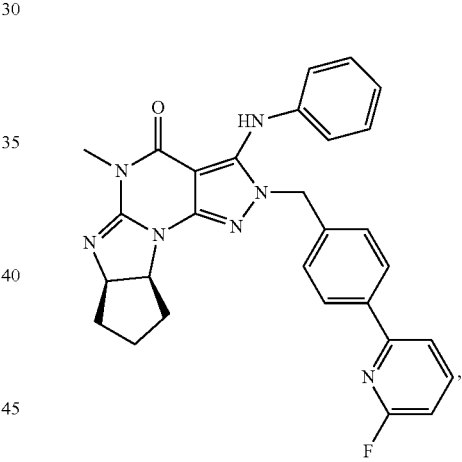

in free or salt form.

6. A method of claim 5, wherein the administration of the PDE1 inhibitor replenishes, replaces, and/or supplements neurons and/or glial cells.

7. A method of claim 1, wherein the CNS disease, disorder, or injury is selected from the group consisting of: retinal injury or trauma, glaucoma, frontotemporal dementia, dementia with Lewy bodies, corticobasal degeneration, progressive supranuclear palsy, prion disorders, multiple system atrophy, amyotrophic lateral sclerosis, hereditary spastic paraparesis, spinocerebellar atrophies, friedreich's ataxia, amyloidoses, diabetic neuropathy, chronic CNS inflammation, and Charcot Marie tooth disease.

8. A method of claim 1, wherein the CNS disease disorder, or injury is retinal injury or trauma.

9. A method of claim 1, wherein the CNS disease disorder, or injury is glaucoma.

10. A method of claim 1, wherein the CNS disease disorder, or injury is dementia with Lewy bodies.

11. A method of claim 1, wherein the CNS disease disorder, or injury is a metabolic (diabetes) related disorder.

12. A method of claim 1, wherein the CNS disease disorder, or injury is diabetic neuropathy.

13. A method of claim 1, wherein the CNS disease disorder, or injury is chronic CNS inflammation.

* * * * *